United States Patent [19]
Conner et al.

[11] Patent Number: 5,579,393
[45] Date of Patent: Nov. 26, 1996

[54] SYSTEM AND METHOD FOR SECURE MEDICAL AND DENTAL RECORD INTERCHANGE

[75] Inventors: Guy Conner; Larry Schmier, both of Santa Rosa, Calif.

[73] Assignee: EScan, Inc., Santa Rosa, Calif.

[21] Appl. No.: 263,143

[22] Filed: Jun. 21, 1994

[51] Int. Cl.$^6$ ............................................. H04L 9/00
[52] U.S. Cl. .................................. 380/25; 380/4; 380/23; 380/24; 380/49; 380/50; 364/413.01; 364/413.02; 364/413.13; 364/413.28
[58] Field of Search .................................. 380/3, 4, 5, 23, 380/24, 25, 30, 49, 50, 54; 340/825.31, 825.34; 364/401, 413.01, 413.02, 413.13, 413.28

[56] References Cited

U.S. PATENT DOCUMENTS

| | | | |
|---|---|---|---|
| 4,907,274 | 3/1990 | Nomura et al. | 380/30 |
| 5,319,543 | 6/1994 | Wilhelm | 364/401 |

OTHER PUBLICATIONS

"Answers to Frequently Asked Questions About Today's Cryptography"; (Rev. 2.0; RSA Data Security, Inc; Oct. 5, 1993); no author named.

*Primary Examiner*—Bernarr E. Gregory
*Attorney, Agent, or Firm*—Carr, DeFilippo & Ferrell LLP

[57] ABSTRACT

A system for secure medical and dental record interchange comprises a provider system and a payer system. The provider system includes a digital imager, a processing unit, a data transmission/reception device, and a memory having a provider management unit and a security unit. For each image acquired from the digital imager, the provider management unit generates a unique image ID, and creates an image relation structure having a source indicator, a status indicator, and a copy-from indicator. The provider management unit organizes images into a message for transmission to a payer system. The security unit performs message encryption, image signature generation, and message signature generation. The payer system includes a processing unit, a data transmission/reception device, and a memory having a payer management unit and a security unit. The payer system's security unit validates message signatures and image signatures received. The payer management unit generates a message rejection notification or a message acceptance notification. A method for provider-side secure medical and dental record interchange comprises the steps of: acquiring an image; generating a unique image ID and an image relation structure; maintaining a status indicator, a source indicator, and a copy-from indicator; generating an image signature; creating a message that includes the image; and generating a message signature. A method for payer-side secure medical and dental record interchange comprises the steps of: validating a message signature; validating an image signature; and selectively generating a message acceptance notification or a message rejection notification.

26 Claims, 21 Drawing Sheets

SYSTEM AND METHOD FOR SECURE MEDICAL AND DENTAL RECORD INTERCHANGE

BACKGROUND OF THE INVENTION

1. Field of the Invention

The present invention relates generally to systems and methods for electronic data interchange, and more particularly to systems and methods for data monitoring and data authentication. Still more particularly, the present invention is a system and method for secure medical and dental record interchange.

2. Description of the Background Art

When a medical professional such as a doctor or a dentist performs services related to a given patient, a record that includes medical or dental information, respectively, associated with the patient is generated. This medical information can include one or more X-rays, dental charts, treatment plans, clinical notes, or other information. Generally, the medical professional, or provider, must send a claim to an insurance company or other medical claim payment authority for a review. As a part of the review, the provider may be required to send supporting medical information associated with the claim to the medical claim payment authority. During the review, the medical claim payment authority may attempt to determine the condition of the patient and whether a proposed or undertaken treatment is appropriate. Based upon the review, the medical claim payment authority may or may not authorize payment for the associated medical services. In the event that the claim is sent to a Health Maintenance Organization (HMO), the aforementioned review is typically performed prior to the authorization of a proposed treatment.

The use of electronic systems and methods, and in particular computer systems and computer-based methods, for the generation, acquisition, and storage of medical information is becoming increasingly common. For example, digital X-ray devices are often used to generate digital X-ray images. As another example, a digital image representing nearly any type of document or picture can be generated via a scanning device. After a digital image has been generated or acquired, the image can be stored on a computer system's hard disk drive or optical disk drive. As yet another example, clinical notes or treatment recommendations can be entered via a word processing program and stored within a data file. The use of computer systems and computer-based methods for medical and dental claim processing is highly desirable because such systems and methods offer the promise of reduced claim processing costs and near-real-time claim review.

Associated with each piece of medical information sent to a medical claim payment authority is a risk of fraud. In particular, the medical claim payment authority may have no indication whether one or more portions of a given patient's medical information have been altered, or whether the medical information that has been submitted actually corresponds to the indicated patient. The use of computer systems and computer-based methods for generating, storing, and transmitting medical information increases the risk of fraud because digital data can be easily manipulated, modified, or copied. In the prior art, no system or method exists for reducing the risk of fraud when medical or dental information is generated or acquired electronically.

In data processing applications, systems and methods for the prevention of fraud fall within the topic of data security.

What is needed is a means for medical and dental record interchange that reduces the risk of fraud when medical and dental information is generated, acquired, or transmitted electronically.

SUMMARY OF THE INVENTION

The present invention is a system and method for secure medical and dental record interchange. The system of the present invention comprises at least one provider system and a payer system. Each provider system is associated with one or more medical service providers within a medical service provider group. The payer system is associated with a medical claim payment authority. Those portions of the present invention associated with a provider system are referred to herein as being on a "provider-side." In a like manner, those portions of the present invention associated with a payer system are referred to herein as being on a "payer-side."

Each provider system comprises a digital imager, a processing unit, a data transmission/reception device, and a memory having a provider management unit, a security unit, an image memory, and a communications memory. The digital imager can be any source from which a digital image can be obtained, including a digital X-ray device, a camera, a scanner, or a data file. The provider management unit directs the acquisition of medical information that includes one or more images obtained via the digital imager. Once an image has been acquired, the provider management unit generates a unique image identification (ID) corresponding to the image, and sets initial values for a status indicator, a source indicator, and a copy-from indicator within a provider-side image relation structure. The status indicator, the source indicator, and the copy-from indicator reflect a manner in which the image was acquired, the device from which the image was acquired, and whether the image is a copy or an original. The provider management unit additionally maintains the values of the status indicator, the source indicator, and the copy-from indicator: to reflect any changes in the image after its acquisition.

The security unit provides data encryption and authentication services that facilitate the generation of a digest value and a digital signature for any given data item. When the data item includes an image and its corresponding image ID, the security unit generates an image digest that is a digest value for the combination of the image and the image ID. The security unit additionally encrypts the image digest to generate an image signature.

A transmission from a provider system to a payer system includes one or more messages, where each message contains medical information related to a particular patient. The provider management unit performs transmission operations in response to a transmission request. The transmission request can be generated by the provider system, or can be received from a payer system.

The provider management unit selectively organizes medical information corresponding to a particular patient into a message upon request. Each message provides medical information that is to be reviewed by a medical claim payment authority, and includes at least one image and its corresponding source indicator, status indicator, and copy-from indicator. In a manner analogous to that for an image signature, the security unit generates a message signature upon request. The security unit also encrypts a message upon request.

If a transmission is to be organized into a predetermined format, for example, the ANSI ASC X12 Patient Information Transaction format, the provider management unit organizes the transmission into the required format upon request. Via the data transmission/reception device, the provider management unit sends the transmission to a specified payer system upon request or as part of a standard procedure.

The payer system comprises a processing unit, a data transmission/reception device, and a memory having a payer management unit, a security unit, and a communications memory. As mentioned above, the payer system can issue a transmission request to a particular provider system, thereby requesting medical information associated with one or more patients. Via the payer system's data transmission/reception device, the payer system receives a transmission that includes one or more messages from a provider system. Upon receiving the transmission, the payer management unit removes any predetermined format that had previously been applied to the transmission, such as the ANSI ASC X12 Patient Information Transaction format.

The security unit within the payer system decrypts any encrypted messages within the transmission, validates the authenticity of messages for which a message signature has been generated, and validates the authenticity of images for which an image signature has been generated. For each message within the transmission, the payer management unit sends the appropriate provider system a message rejection notification or a message acceptance notification based upon the results of the aforementioned message decryptions, message signature validations, and image signature validations.

A method for provider-side secure medical and dental record interchange comprises the steps of: acquiring an image; updating a status indicator, a source indicator, and a copy-from indicator associated with the image; generating an image signature; performing image display operations; performing message preparation operations; and performing transmission operations.

A method for payer-side secure medical and dental record interchange comprises the steps of: receiving a transmission; decrypting a message; validating a message signature; validating an image signature; sending a message acceptance notification in the event that a message has been successfully decrypted, a required message signature has been successfully validated, and any required image signatures within the message have been successfully validated; and sending a message rejection notification in the event that a message has not been successfully decrypted, a required message signature has not been successfully validated, or a required image signature within the message has not been successfully validated.

DETAILED DESCRIPTION OF THE PREFERRED EMBODIMENTS

Figure 1:
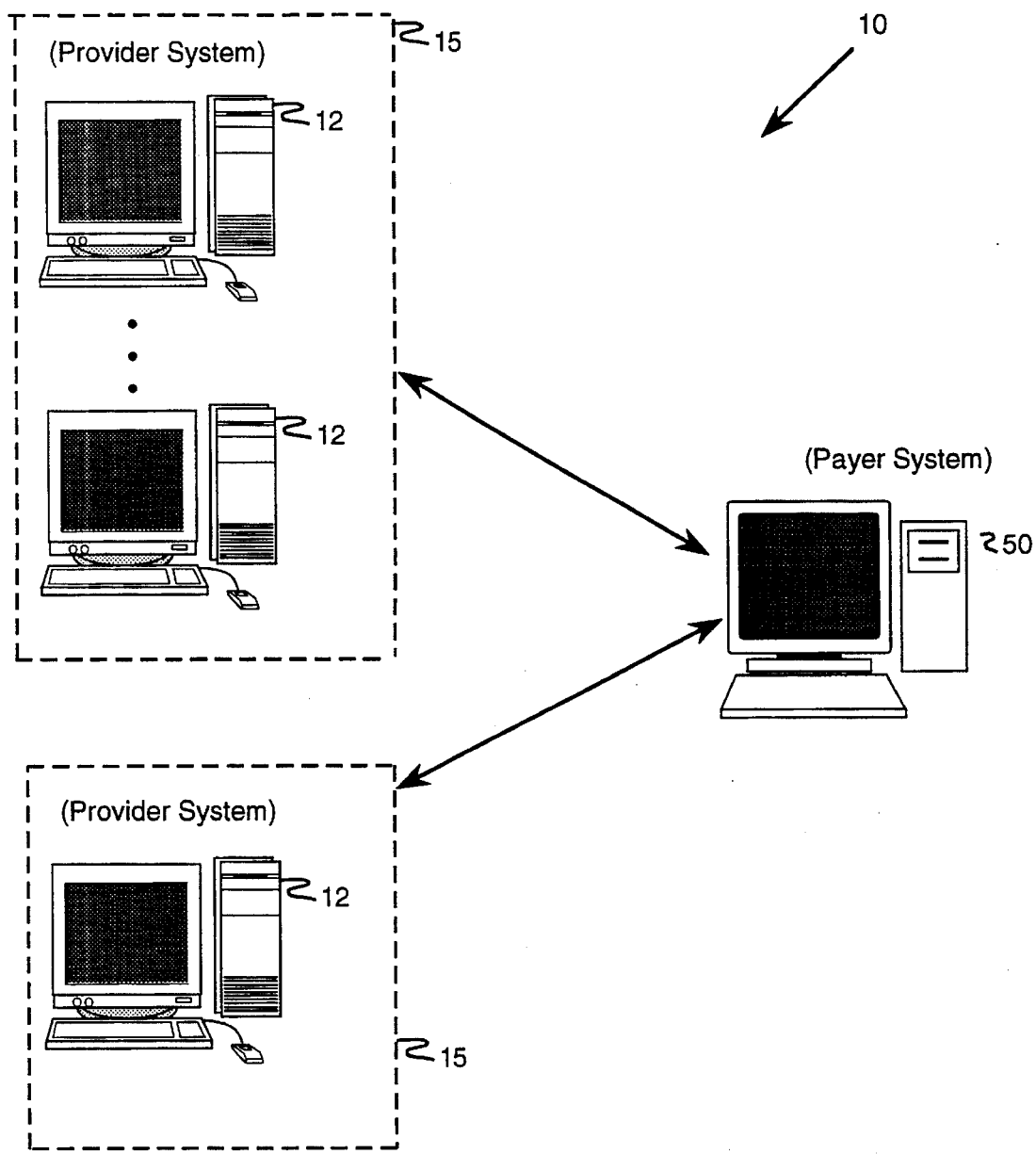
FIG. 1 is a block diagram of a preferred embodiment of a system for secure medical and dental record interchange constructed in accordance with the present invention.

Referring now to FIG. 1, a block diagram of a preferred embodiment of a system 10 for secure medical and dental record interchange constructed in accordance with the present invention is shown. The system 10 for secure medical and dental record interchange comprises at least one provider system 12 and a payer system 50. In the present invention, each provider system 12 is preferably utilized within a medical service provider group 15, for example, a pool of doctors or dentists. Within a given medical service provider group 15, each individual medical professional having patient diagnosis and treatment responsibility is referred to herein as a provider. The provider system 12 collects, processes, and stores medical information, or a medical record, related to one or more patients associated with the medical service provider group 15. Preferably, the medical information includes one or more X-rays and possibly clinical notes, medical or dental charts, or other patient-related data. In the preferred embodiment, the medical information can be in a variety of formats, including pixel format, ASCII format, or in a text-based format particular to a word-processing program such as Microsoft Word. Those skilled in the art will recognize that in general, the present invention supports any format for the medical information.

The payer system 50 is preferably utilized within a medical claim payment authority such as a medical insurance company. Herein, a medical claim payment authority is referred to as a payer. The system 10 for medical record interchange security facilitates the collection, transfer, and authentication of medical information between a provider and a payer.

In the present invention, medical information associated with one or more patients is transferred from a provider system to a payer system for evaluation and processing upon request or as a part of a standard procedure. Portions of the present invention associated with a provider system are referred to herein as being on the "provider side," and portions of the present invention associated with a payer system are referred to as being on the "payer side."

Figure 2A:
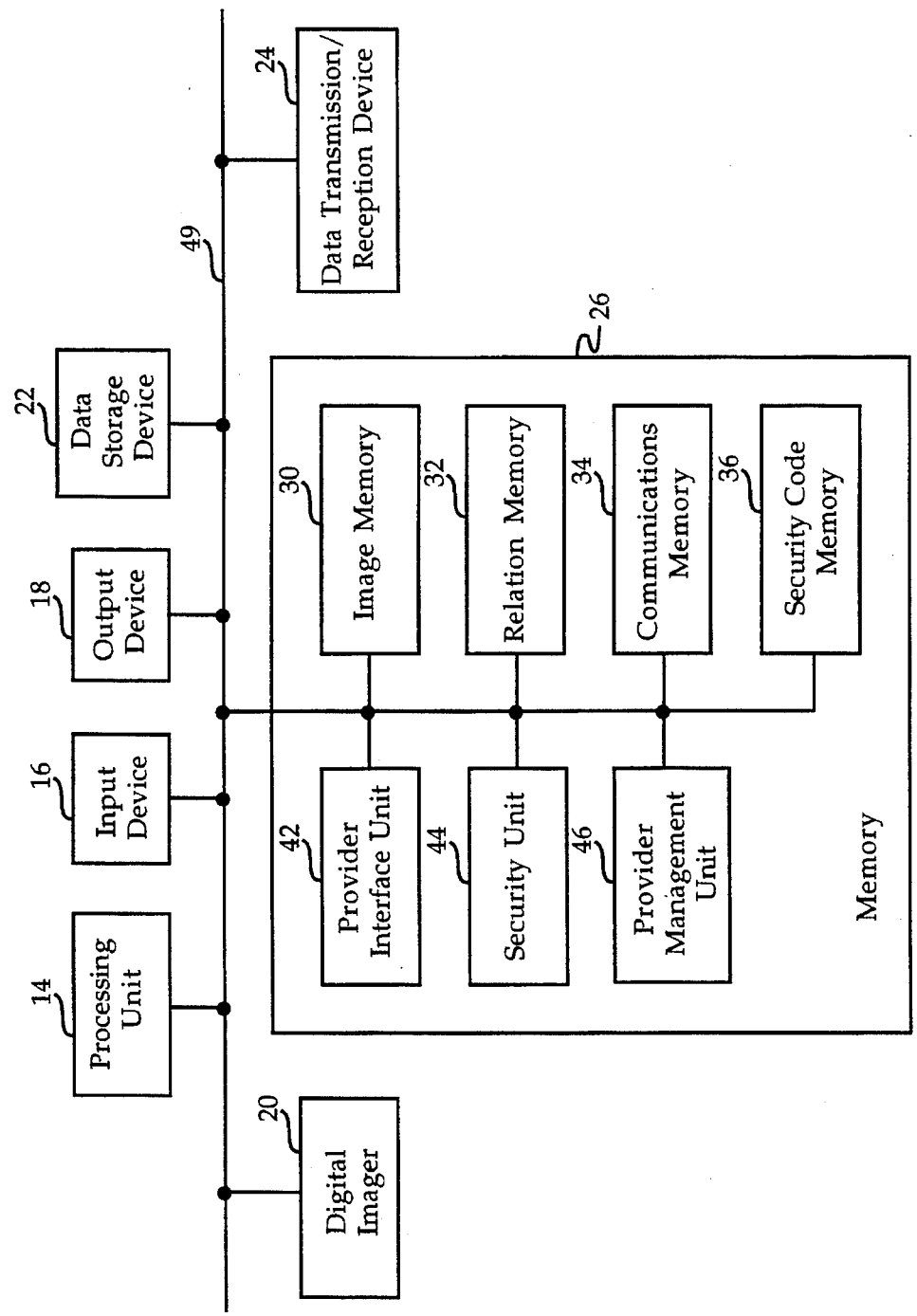
FIG. 2A is a block diagram of a provider system of the present invention.

Referring also now to FIG. 2A, a block diagram of a preferred embodiment of a provider system 12 is shown. The provider system 12 preferably comprises a processing unit 14, an input device 16, an output device 18, at least one digital imager 20, at least one data storage device 22, a data transmission/reception device 24, and a memory 26 having an image memory 30, a relation memory 32, a communications memory 34, a security code memory 36, a provider interface unit 42, a security unit 44, and a provider management unit 46. Each element of the provider system 12 has an input and an output coupled to a common provider system bus 49.

In the present invention, the digital imager 20 can be any source from which a digital image can be obtained. In the preferred embodiment, the digital imager 20 can be a digital X-ray unit, a scanner, a camera, or a data file that contains a digital image. Those skilled in the art will recognize that the digital imager 20 may also be an analog image source coupled to an image capture device such as a "frame grabber" card. Those skilled in the art will also recognize that the present invention can be used with any type of data storage device 22 in general, including an optical disk drive or a magnetic tape drive. The data transmission/reception device 24 can be a modem coupled to a telephone line, a coupling to a network, or any other means for providing data communication between computers.

In an exemplary embodiment, the provider system 12 is a digital X-Ray device, scanner, or camera coupled to a personal computer system having an Intel 80486 microprocessor, a 540 Mbyte hard disk drive, a modem, and 16 Megabytes of Random Access Memory (RAM) wherein the image memory 30, the relation memory 32, the communications memory 34, the security code memory 36, the provider interface unit 42, the security unit 44, and the provider management unit 46 reside.

The provider interface unit 42 provides a set of menus that form a user interface for entering data and commands on the provider system 12. The provider interface unit 42 translates user input into requests directed to the security unit 44 and the provider management unit 46. In the preferred embodiment, the provider interface unit 42 is a sequence of computer program steps stored in the memory 26.

The security unit 44 facilitates data encryption and data authentication services. In the preferred embodiment, the security unit 44 is a sequence of computer program steps residing within the memory 26 and based upon public-key/private-key cryptography. In public-key/private-key cryptography, each user within a group of users is assigned a unique public key anti a corresponding unique private key. A given public key is a code associated with a particular user that is available to other users via a directory. A private key is a code associated with a particular user and thereby with a corresponding public key, and is kept secret. In an exemplary embodiment, the security unit 44 is a sequence of computer program steps based upon the RSA cryptosystem, as described in U.S. Pat. No. 4,405,829 and supplied by RSA Data Security, Inc., of Redwood City, Calif. Those skilled in the art will recognize that the security unit 44 could be based upon various other cryptography systems in an alternate embodiment.

Figure 3A:
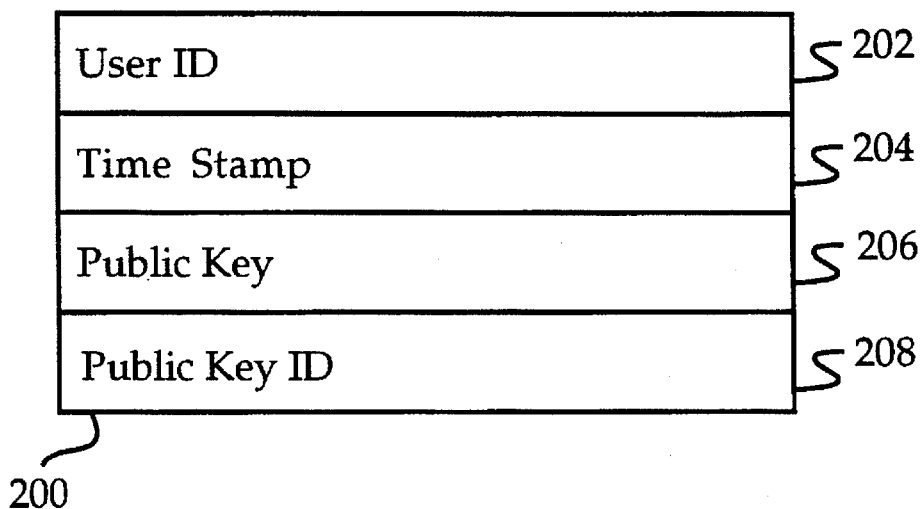
FIG. 3A is a block diagram of a public key structure of the present invention

The security unit 44 creates a unique public key and a corresponding unique private key for each provider system user within a medical service provider group 15 in response to a key creation request. In the preferred embodiment, each public key and each corresponding private key is a binary number having from 64 to 256 bits. A given public key and the corresponding private key are referred to herein as a key pair. For each public key and private key created, the security unit 44 creates a respective public key structure 200 and private key structure 220. Referring now to FIG. 3A, a block diagram of a preferred embodiment of a public key structure 200 is shown. The public key structure 200 is a data structure having a first data field 202 for storing a user identification (ID) corresponding to the provider system user; a second data field 204 for storing a time stamp that specifies the date and the time the public key was created; a third data field 206 for storing the actual public key; and a fourth data field 208 for storing a public key ID comprising a subset of the bits within the public key. The set of public key structures associated with a particular medical service provider group 15 is referred to herein as a public key ring.

Figure 3B:
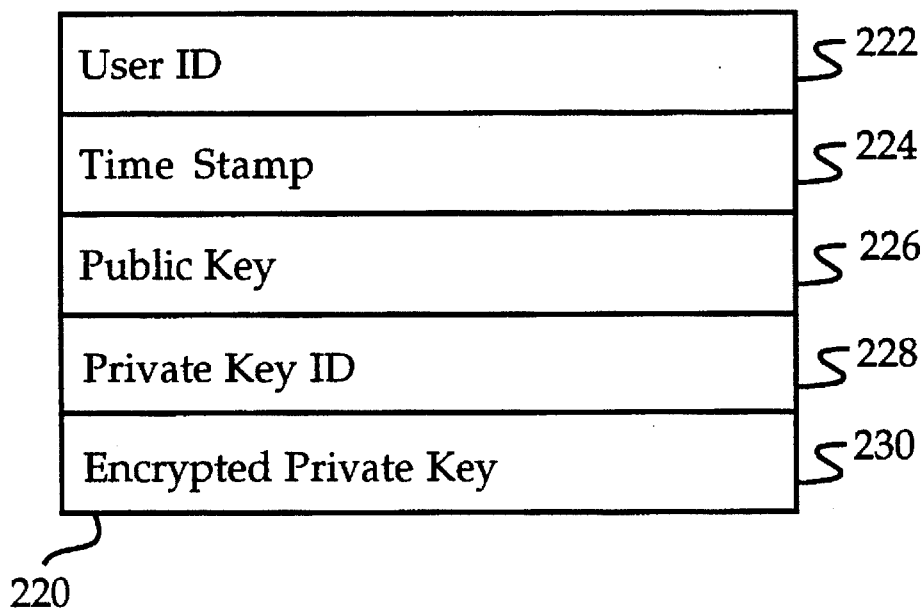
FIG. 3B is a block diagram of a private key structure of the present invention.

Referring now to FIG. 3B, a block diagram of a preferred embodiment of a private key structure 220 is shown. The private key structure 220 is a data structure having a first data field 222 for storing the user ID specified in the corresponding public key structure 220; a second data field 224 for storing the time stamp specified in the corresponding public key structure; a third data field 226 for storing the private key itself; a fourth data field 228 for storing a private key ID comprising a subset of bits within the private key; and a fifth data field 230 for storing the private key in an encrypted form, the encryption occurring according to a password associated with the provider. In the preferred embodiment, the set of private key structures associated with a medical service provider group 15 is referred to herein as a private key ring. In the preferred embodiment, each public key structure 200 and each private key structure 220 is created in the security code memory 36, and stored in the security code memory 36 and on the data storage device 22. The security unit 44 preferably makes each public key ID, and thereby each public key, known to provider system users and to payer system users via a directory. As will be described in detail below, each payer system 50 has a security unit 44 that functions in a manner analogous to the provider system's security unit 44.

The security unit 44 generates a digital signature, which facilitates later data authentication, in response to a signature generation request issued by a particular provider system user. Preferably, the signature generation request specifies a data item that may require authentication at a later time and the private key of the provider system user that issued the signature generation request. Herein, the provider system user that issues a signature generation request is referred to as a "signer," and a data item for which a digital signature has been generated is referred to as being "signed." Following receipt of the signature generation request, the security unit 44 generates a number referred to herein as a digest value that uniquely identifies the data item. The digest value is created via a one-way strong cryptographic hashing function applied to the data item. Following the creation of the digest value, the security unit 44 encrypts the digest value with the specified private key, as will be described in more detail below. The encrypted digest value is the digital signature.

The security unit 44 also verifies a digital signature, and in so doing verifies the authenticity of a data item, in response to a verification request. Preferably, the verification request specifies a data item, a previously-generated digital signature for the data item, and a public key corresponding to the private key used to generate the data item's digital signature. In response to the verification request, the security unit 44 first calculates the digest value for the data item. The security unit 44 then decrypts the previously-generated digital signature using the public key specified in the verification request, thereby obtaining the original digest value for the data item. The security unit 44 next compares the original digest value with the newly-calculated digest value; if the two values are equal, the data item has not been modified. If the two digest values are not equal, the data item has been modified and is not authentic.

Figure 4:
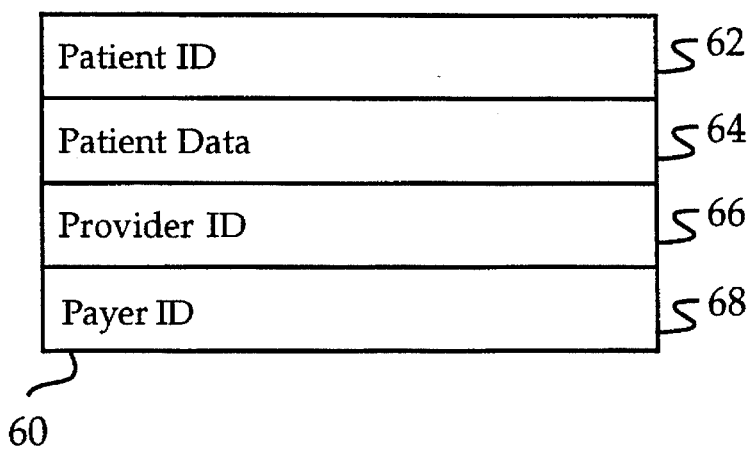
FIG. 4 is a block diagram of a patient relation structure of the present invention.

The provider management unit 46 creates and manages data structures within the provider system 12 as will be described below. In the preferred embodiment, the provider management unit 46 is a sequence of computer program steps residing within the memory 26. In response to a new patient request, the provider management unit 46 creates a patient relation structure 60. Referring now to FIG. 4, a block diagram of a preferred embodiment of a patient relation structure 60 is shown. The patient relation structure 60 is a data structure having a first data field 62 for storing a unique patient ID; a second data field 64 for storing patient-related data including the patient's name, age, sex, and most recent examination date; a third data field 66 for storing a provider ID that uniquely identifies an individual provider associated with the patient; and a fourth data field 68 for storing a payer ID corresponding to a medical insurer.

The provider management unit 46 also modifies or deletes a patient relation structure 60 in response to a patient data modification command or patient deletion command, respectively. Preferably, each patient relation structure 60 is created in the relation memory 32, and stored on the data storage device 22. As will be described below, the provider user interface 42 may require information specified in the patient relation structure 60 prior to the transmission of information to a payer. When the patient relation structure 60 is being modified or used for other purposes, the patient relation structure 60 preferably resides within the relation memory 32.

Figure 5:
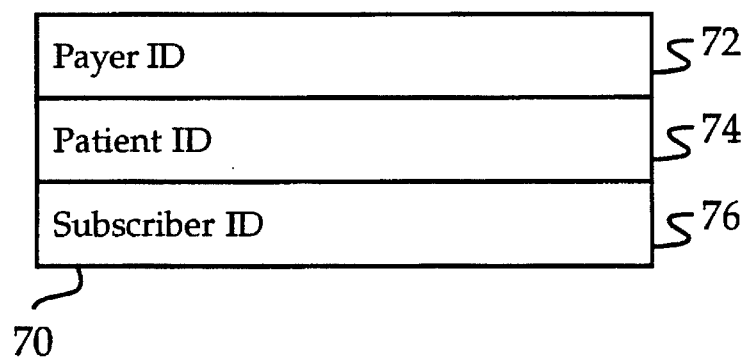
FIG. 5 is a block diagram of a payer relation structure of the present invention.

When a patient relation structure 60 is created, modified, or deleted, the provider management unit 46 also respectively creates, modifies, or deletes a corresponding payer relation structure 70. The provider management unit 46 may also respectively create, modify, or delete a corresponding provider relation structure 80. Referring now to FIG. 5, a block diagram of a preferred embodiment of a payer relation structure 70 is shown. The payer relation structure 70 is a data structure having a first data field 72 for storing the payer ID specified in the patient relation structure 60; a second data field 74 for storing the patient ID specified in the patient relation structure 60; and a third data field 76 for storing a subscriber ID in the event that the patient's medical insurance is provided by another person, for example, a parent. In the preferred embodiment, the creation and storage locations of the payer relation structure 70 correspond to the respective creation and storage locations of the associated patient relation structure 60.

Figure 6:
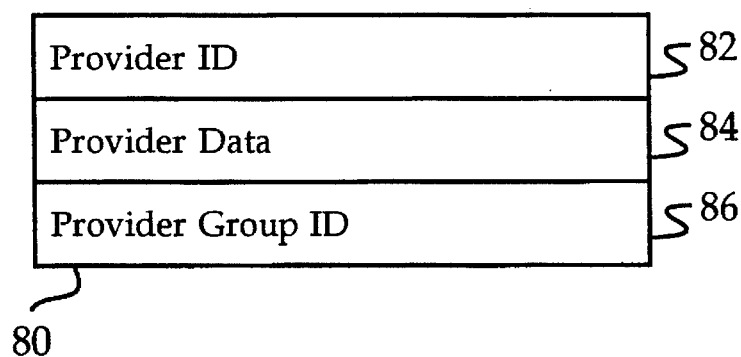
FIG. 6 is a block diagram of a provider relation structure of the present invention.

In response to a new provider request, the provider management unit 46 creates a provider relation structure 80. Referring now to FIG. 6, a block diagram of a preferred embodiment of a provider relation structure 80 is shown. The provider relation structure 80 is a data structure corresponding to an individual provider and having a first data field 82 for storing a unique provider ID; a second data field 84 for storing provider-related data such as the provider's name and the state in which the provider is licensed to practice; and a third data field 86 for storing a unique provider group ID corresponding to the medical service provider group 15 within which the provider functions. In a manner analogous to the patient relation structure 60, the provider management unit 46 also modifies or deletes a provider relation structure 80 in response to a provider data modification command or a provider deletion command, respectively. In the preferred embodiment, the new provider request, the provider data modification command, and the provider deletion command are selectively and automatically issued by the provider management unit 46 in response to corresponding new patient command, a patient data modification command, or a patient deletion command, respectively. Preferably, the provider relation structure 80 is created in the relation memory 32, and resides within the relation memory 32 when being modified or when being used for other purposes as will be described below. Otherwise, the provider relation structure 80 preferably resides on the data storage device 22.

In response to an image acquisition command issued by a provider system user that specifies a patient ID and a digital imager 20, the provider management unit 46 digitizes, captures, or acquires a digitized medical image from the specified digital imager 20. If the digital imager 20 is a data file, the data file can be stored in the provider system's memory 26; on the provider system's data storage device 22; on another provider system 12; or on a device or system not associated with any provider system 12. Those skilled in the art will recognize that the present invention is applicable to any type of digital medical image acquired from any type of digital imager 20. Hereafter, the digitized medical image is referred to as the image.

Figure 7:
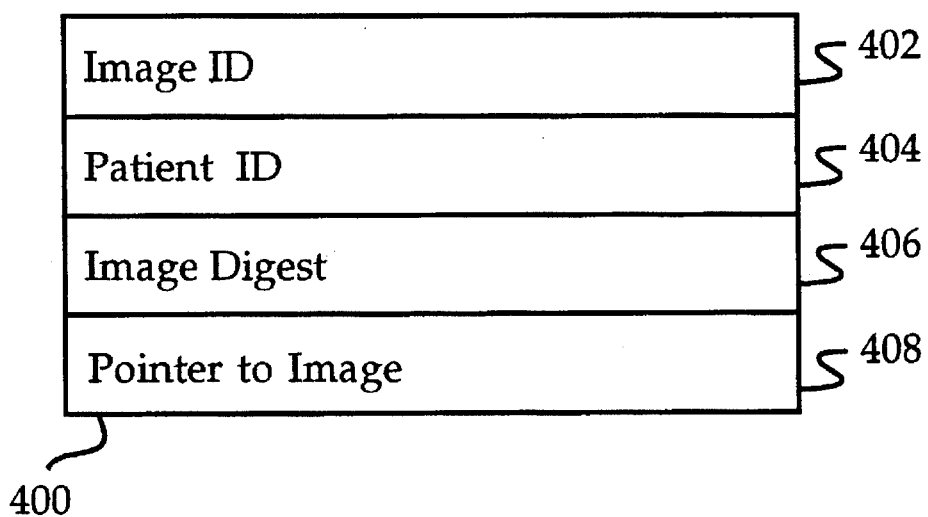
FIG. 7 is a block diagram of an image header structure of the present invention.

Initially, the image is stored in the image memory 30 after its acquisition. Once the image has been stored in the image memory 30, the provider management unit 46 generates an image ID that uniquely identifies the image. In the preferred embodiment, the image ID includes a unique provider system serial number, the date on which the image was acquired, and the time at which the image was acquired. After generating the image ID, the provider management unit 46 creates an image header structure 400 corresponding to the image. Referring now to FIG. 7, a block diagram of a preferred embodiment of an image header structure 400 is shown. The image header structure 400 is a data structure having a first data field 402 for storing the image ID corresponding to the image; a second data field 404 for storing the patient ID specifying the patient with which the image is associated; a third data field 406 for storing a digest value obtained from the combination of the image and the contents of the first and second data fields 402, 404 of the image header structure 400, and referred to herein as an image digest; and a fourth data field 408 for storing a pointer to the image. In the preferred embodiment, the provider management unit 46 initially stores the image and the image header structure 400 in a standard TIFF file format in the image memory 30.

Figure 8A:
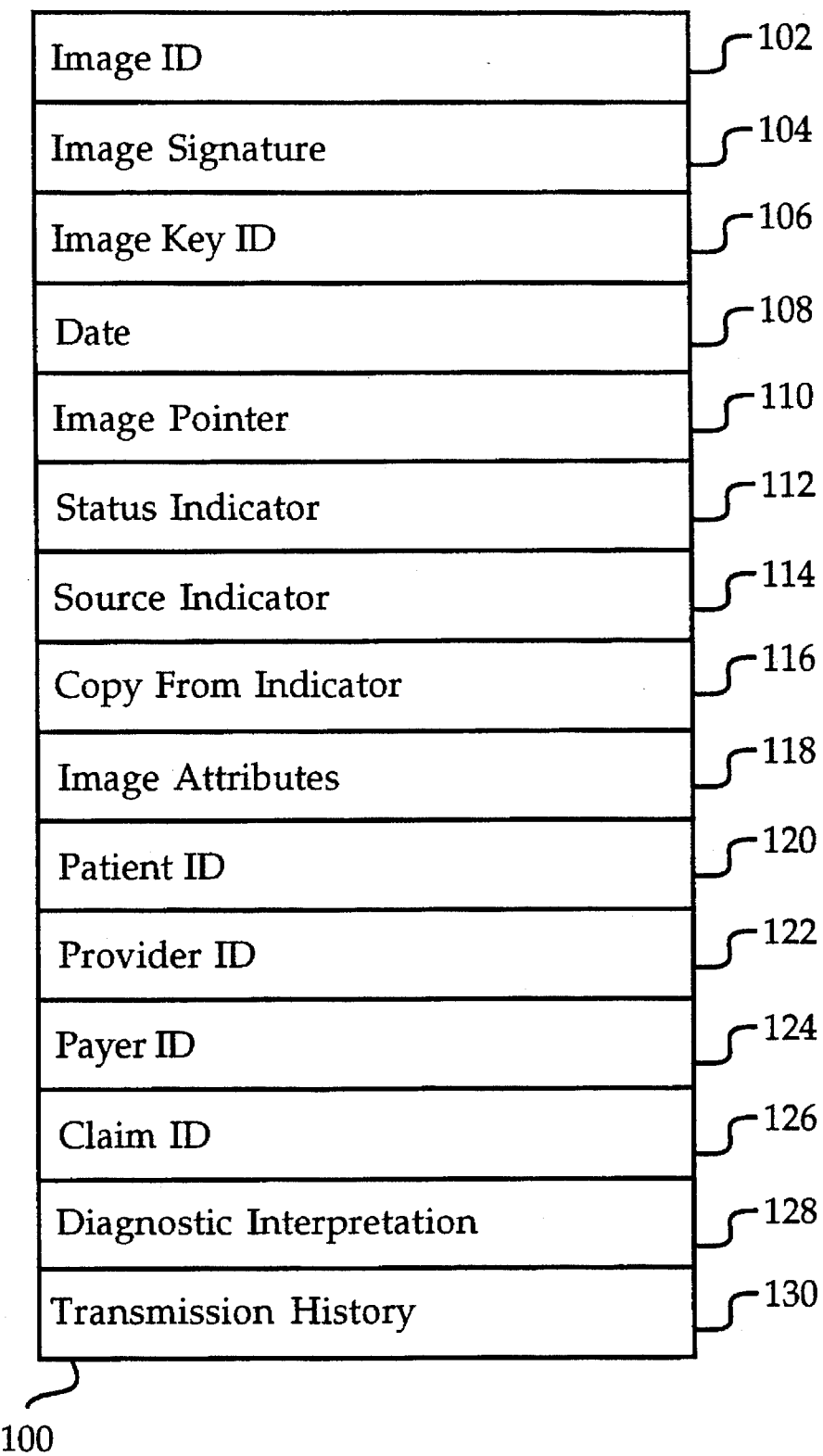
FIG. 8A is a block diagram of a provider-side image relation structure of the present invention.

After creating the image header structure 400, the provider management unit 46 creates a corresponding provider-side image relation structure 100. Referring now to FIG. 8A, a block diagram of a preferred embodiment of a provider-side image relation structure 100 is shown. The provider-side image relation structure 100 is a data structure having a first data field 102 for storing the image ID associated with the image; a second data field 104 for storing a digital signature generated from the combination of the image and the contents of the image header structure 400 using the decrypted private key stored in the provider system user's public key structure 220, and referred to herein as an image signature; a third data field 106 for storing an image key ID comprising a subset of bits from the public key of the provider associated with the patient; a fourth data field 108 for storing the date upon which the image was signed; a fifth data field 110 for storing an image pointer that points to the location at which the corresponding TIFF file containing the image and the image header structure 400 is stored; a sixth data field 112 for storing a status indicator that specifies a categorization of the image according to whether the image is an original or a copy; a seventh data field 114 for storing a source indicator that specifies the image source from which the image was originally acquired; an eighth data field 116 for storing a copy-from indicator that specifies whether the image is a copy, and that specifies a copy source in the event that the image is a copy; an ninth data field 118 for storing a set of image attributes such as image resolution and scale of measurement; a tenth data field 120 for storing the patient ID specified in the image acquisition command; an eleventh data field 122 for storing the provider ID associated with the specified patient ID; a twelfth data field 124 for storing the payer ID associated with the patient ID; a thirteenth data field 126 for storing a claim ID corresponding to an insurance claim; a fourteenth data field 128 for storing an optional diagnostic interpretation associated with the image; and a fifteenth data field 130 for storing a transmission history that specifies a date and a time at which the image was most-recently transmitted. The image relation 100 is initially created and stored in the relation memory 32.

The provider management unit 42 sets the initial contents of the sixth through eighth data fields 112, 114, 116 of the provider-side image relation structure 100 according to the specified digital imager 20. In the preferred embodiment, the sixth data field 112, containing the status indicator, is initially assigned a value of "primary original," "secondary original," or "copy." A primary original corresponds to the digital imager 20 being: a digital X-ray device; a secondary original corresponds to the digital imager 20 being a camera or a scanner; and a copy corresponds to the digital imager 20 being a data file. Those skilled in the art will recognize that other categorizations of the image as provided by the status indicator could be provided in an alternate embodiment.

In the preferred embodiment, the provider-side image relation structure's seventh data field 114, containing the source indicator, is initially assigned a value of "digital X-ray," "camera," "scanner," or "file," corresponding to whether the specified digital imager 20 is a digital X-ray device, a camera, a scanner, or a data file, respectively. The eighth data field 116 in the provider-side image relation structure 100, containing the copy-from indicator, is assigned a value of "digital X-ray," "camera," or "scanner" in the event that the digital imager 20 is a digital X-ray device, a camera, or a scanner, respectively; or the filename corresponding to the file from which the image has been copied from in the event that the digital imager 20 is a data file.

After the image has been transferred from the digital imager 20 into the image memory 30 and after the image header structure 400 and the provider-side image relation structure 100 have been created, the provider management unit 46 displays the image on the output device 18. The provider management unit 46 provides image clipping operations, image modification operations, and image manipulation operations upon request. In the image clipping operations, an unmodified subset of the bits comprising the original image are selected as a new image. The image modification operations include contrast enhancement, image negation, and zoom factor specification. The image manipulation operations include flip, rotate, and mirror. Those skilled in the art will recognize that other image modification operations and image manipulation operations could be provided in an alternate embodiment.

As the image is clipped or modified, the provider management unit 46 updates the corresponding provider-side image relation structure 100 to reflect the clipping or the manner in which the image has been modified, respectively. In particular, if the image is a primary original or a secondary original and has been clipped, the provider management unit 46 sets the value of the status indicator in the provider-side image relation structure's sixth data field 112 to "clipped original." If the image has been modified, the provider management unit 46 assigns the status indicator a value of copy. When an image has been clipped or modified, the provider management unit 46 saves the image and the corresponding updated provider-side image relation structure 100 as a new image and a new provider-side image relation structure 100, respectively, having a new image ID. In the preferred embodiment, the provider-side image relation structure 100 is initially stored in the relation memory 32.

Via the generation of the image ID and the setting and maintenance of the status indicator, the source indicator, and the copy-from indicator, the present invention advantageously provides a means for reducing the risk of fraud associated with: 1) the manner in which an image has been acquired, and 2) a manner in which an image has been altered after its acquisition. Additional means provided by the present invention for reducing the risk of fraud in a medical or dental record transaction are discussed in detail below.

After capturing the image, generating the image ID, creating the provider-side image relation structure 100, and facilitating image clipping, image modification, and image manipulation operations, the provider management unit 46 determines whether an image signature is to be generated for the image. The image signature provides a means for a provider to attest to the authenticity of the image. In the event that an image signature is to be generated, the security unit 44 first generates the image digest from the combination of the image and the contents of the first and second data fields 402, 404 of the image header structure 400. The provider management unit 46 stores the image digest in the third data field 406 of the image header structure 400 associated with the image. Next, the security unit 44 encrypts the image digest with the private key associated with the provider system user that is attesting to the authenticity of the image. The provider management unit 44 stores the image signature in the provider-side image relation structure's second data field 104.

In response to an image storage request, the provider management unit 46 stores the TIFF file containing the image header structure 400 and the image on the data storage device 22. The provider management unit 46 also updates the fifth data field 110 within the provider-side image relation structure 100, and stores the provider-side image relation structure 100 on the data storage device 22 as well.

The provider management unit 46 displays an image on the output device 18 in response to a view image request that specifies an image ID. In response to the view image request, the provider management unit 46 first locates the image corresponding to the specified image ID. If the image is not already present in the image memory 30 but is stored on the data storage device 22, the provider management unit 46 retrieves the image from the data storage device 22 and loads the image into the image memory 30. Once the image is present in the image memory 30, the provider management unit 46 displays the image on the output device 18. The provider management unit 46 next provides the aforementioned set of image clipping operations, image modification operations, and image manipulation operations upon request for altering the contents or the appearance of the image. When the image is clipped or modified, the provider management unit 46 updates the contents of the provider-side image relation structure 100 as described above, and stores the image and the updated provider-side image relation structure 100 as a new image having a new provider-side image relation structure 100 upon request.

In the present invention, a transmission from a provider system 12 to a payer system 50 includes one or more messages, where each message comprises a set of images and the image header structure 400 associated with each image; an image attachment structure 140 associated with each image and described in detail below; and a message header structure 180 as will be described in detail below. Each message is associated with a particular patient:. In response to a message preparation request issued by a preparing provider system user who specifies an image or a group of images, the provider management unit 46 loads each image and each corresponding image header structure 400 associated with each specified image ID into the communications memory 34. For each image, the provider management unit 46 creates an image attachment structure 140.

Figure 9:
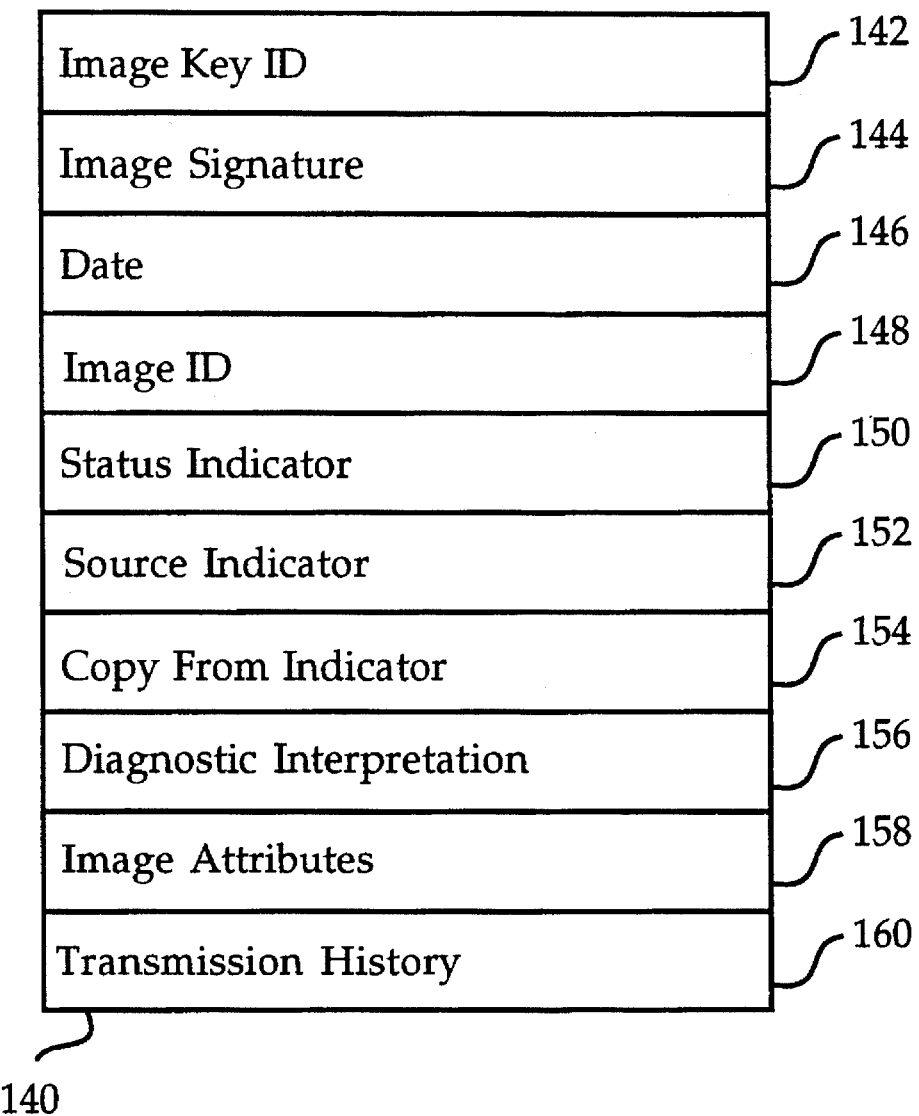
FIG. 9 is a block diagram of an image attachment header structure of the present invention.

Referring now to FIG. 9, a block diagram of a preferred embodiment of an image attachment structure 140 is shown. The image attachment structure 140 is a data structure created from the provider-side image relation structure 100 associated with the image and having a first data field 142 for storing the image key ID; a second data field 144 for storing the image signature; a third data field 146 for storing the image signature date; a fourth data field 148 for storing the image ID; a fifth data field 150 for storing the status indicator; a sixth data field 152 for storing the source indicator; a seventh data field 154 for storing the copy-from indicator; an eighth data field 156 for storing the diagnostic interpretation; a ninth data field 158 for storing the image attributes; and a tenth data field for storing the transmission history. In the preferred embodiment, each image attachment structure 140 is stored in the communications memory 34. Following the creation of a given image attachment structure 140, the provider management unit 46 preferably sets the transmission history within the appropriate provider-side image relation structure 100 and the image attachment structure 140 to indicate that the image has been transmitted.

Figure 10:
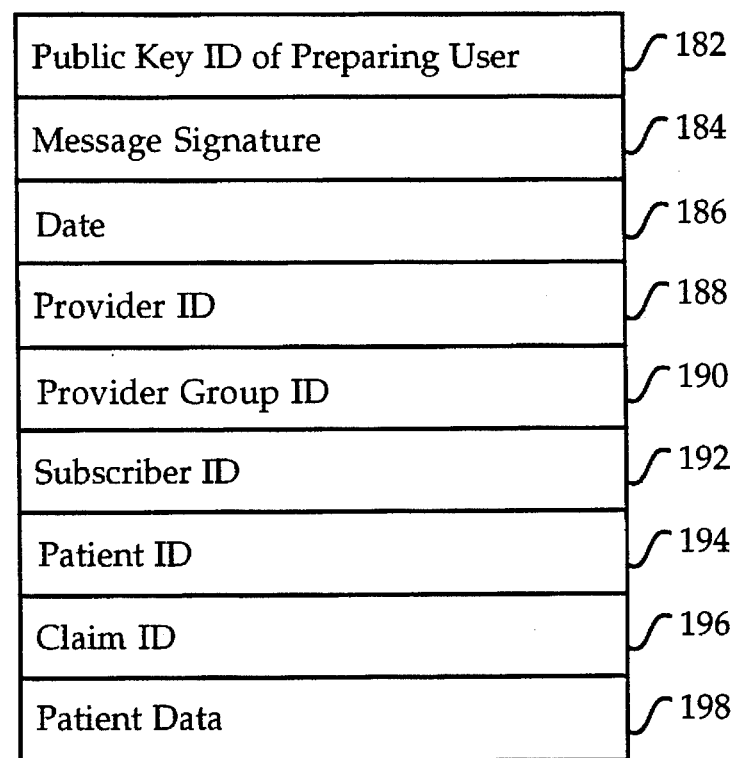
FIG. 10 is a block diagram of a message header structure of the present invention.

After creating an image attachment structure 140 for each image specified in the message preparation request, the provider management unit 46 creates a message header structure 180 corresponding to the specified patient ID. Referring now to FIG. 10, a block diagram of a preferred embodiment of a message header structure 180 is shown. The message header structure 180 is a data structure having a first data field 182 for storing the public key ID corresponding to the specified preparing provider system user; a second data field 182 for storing a message signature, where the message signature is a digital signature associated with the message and described in detail below; a third data field 186 for storing a date upon which the message was signed; a fourth data field 188 for storing the provider ID given in the third data field 66 of the patient relation structure 60 associated with the specified patient ID; a fifth data field 190 for storing the provider group ID associated with the provider ID stored in the preceding data field; a sixth data field 192 for storing the subscriber ID given in the third data field 76 of the payer relation structure 70 associated with the specified patient ID; a seventh data field for storing the specified patient ID; an eighth data field 196 for storing a claim ID; and a ninth data field 198 for storing the patient data contained in the patient relation structure 60 associated with the specified patient ID. In the preferred embodiment, the message header structure 180 is stored in the communications memory 34.

Following the creation of the message header structure 180, the provider management unit 46 determines whether the preparing provider system user has requested that a message signature be generated for the message. If a message signature is to be generated, the security unit 44 first computes a message digest by generating the digest value for the combined contents of each image header structure 400 associated with the message, each image attachment structure 140 associated with the message, and the fourth through the ninth data fields 188, 190, 192, 194, 196, 198 of the message header structure 180. Next, the security unit 44 obtains the private key associated with the preparing provider system user that requested the message signature generation, and encrypts the message digest to obtain the message signature. The provider management unit 46 subsequently stores the private key ID of the preparing provider system user in the message header structure's first data field 182; the message signature itself in the message header structure's second data field 184; and the date upon which the message signature is generated in the message header structure's third data field 186.

After considering the generation of a message signature, the provider management unit 46 directs the security unit 44 in performing message encryption operations in response to an encryption request issued by the preparing provider system user. Preferably, the encryption request specifies a public key ID corresponding to a payer, where the payer's public key ID and corresponding public key is available via a directory maintained by the security unit 44. In the message encryption operations, the security unit 44 encrypts the contents of each image header structure 400, each image attachment structure 140, and the fourth through ninth data fields 188, 190, 192, 194, 196, 198 of the message header structure 180. The encryption is performed using the public key associated with the payer to which the message is to be sent.

In response to a transmission request that specifies a payer ID and an optional format indicator, the provider management unit 46 first determines whether the transmission is to be organized into a predetermined format according to any format indicator specified. Preferably, the predetermined format includes communications protocol information, the transmission, and a structure for the acknowledgment of transmission receipt and transmission processing. In an exemplary embodiment, the predetermined format is the ANSI ASC X12 Patient Information Transaction format. Those skilled in the art will recognize that in an alternate embodiment, a variety of other formats could be supported.

If the transmission is to be organized into a predetermined format, the provider management unit 46 organizes the transmission in accordance with the format. After any transmission formatting has been completed, the provider management unit 46 either sends the contents of the communications memory 34 to the payer system 50 associated with the specified payer ID via the data transmission/reception device 24, or queues the transmission to be sent when a predetermined condition has been satisfied. The queuing of the transmission for sending based upon a predetermined condition facilitates batch transmission involving multiple messages. In the preferred embodiment, the predetermined condition can be a specified time at which to send the transmission, or a minimum transmission size that must be exceeded by the combined sizes of the queued messages. In the present invention, each transmission request is preferably either 1) generated by the provider interface unit 42 in response to a provider action; or 2) received from a particular payer system 50 in the form of a patient information request message as described in detail below.

In response to a message rejection notification received from the payer system 50, the provider management unit 46 logs the message rejection notification in the memory 26. In the preferred embodiment, the message rejection notification specifies a single message that has been rejected by the payer system 50. Thus, for each message that has been rejected by a particular payer system 50, the provider system 12 associated with the message will receive a corresponding message rejection notification. In response to a message acceptance notification received from the payer system 50, the provider management unit 46 logs the message acceptance notification in the memory 26. In a manner similar to that for the message rejection notification, the message acceptance notification specifies a single message that has been accepted by the payer system 50. Thus, for each message that a particular payer system 50 accepts, the provider system 12 associated with the message will receive a corresponding message acceptance notification. The creation of the message rejection notification and the message acceptance notification is described in detail below with reference to FIGS. 20A and 20B.

Figure 2B:
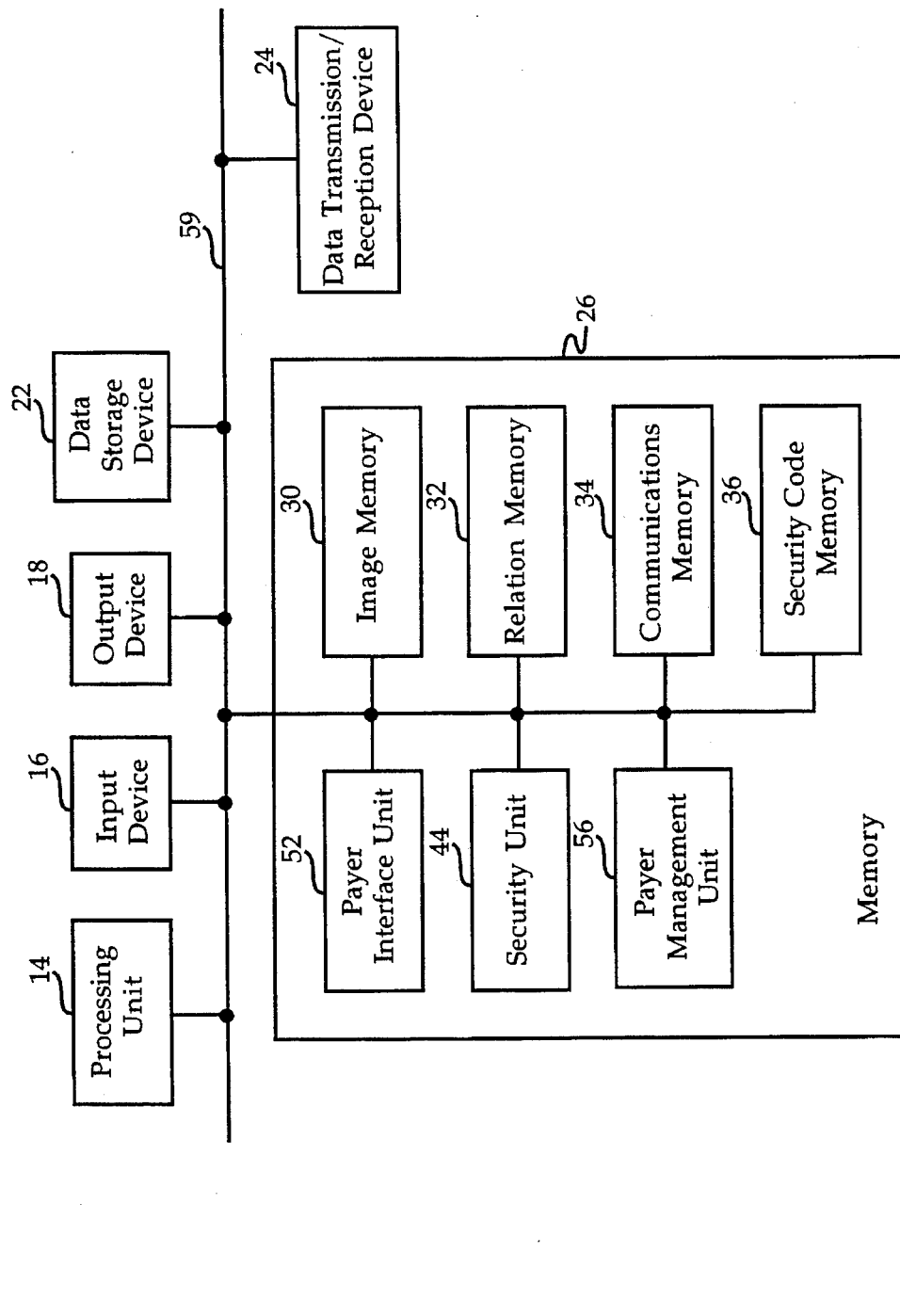
FIG. 2B is a block diagram of a payer system of the present invention.

Referring now to FIG. 2B, a block diagram of a preferred embodiment of a payer system 50 is shown. The payer system 50 has several elements similar to those present in the provider system 12 shown in FIG. 2A. For ease of understanding, like reference numbers have been used for like elements in FIGS. 2A and 2B. The payer system 50 comprises a processing unit 14, an input device 16, an output device 18, an data storage device 22, a data transmission/reception device 24, and a memory 26 having an image memory 30, a relation memory 32, a communications memory 34, a security code memory 36, a payer interface unit 52, a security unit 44, and a payer management unit 56. Each element of the payer system 50 has an input and an output coupled to a common payer system bus 59. In an exemplary embodiment, the payer system 50 is a personal computer system having an Intel 80486 microprocessor, a 540 Mbyte hard disk drive, a modem, and 16 Megabytes RAM wherein the payer system's image memory 30, relation memory 32, communications memory 34, security code memory 36, payer interface unit 52, security unit 44, and payer management unit 56 reside.

The payer interface unit 52 provides a user interface that facilitates the entry of data and commands, and the translation of user actions into requests directed to the payer system's security unit 44 and the payer management unit 56. In response to a user action that specifies a particular provider system 12 as a transmission source, the payer interface unit 52 generates a transmission request that indicates a transmission is required from the specified provider system 12. In the preferred embodiment, the payer interface unit 52 is a sequence of computer program steps stored in the memory 26.

The security unit 44 in the payer system 50 functions in a manner analogous to the security unit 44 in the provider system 12, providing data encryption/decryption operations and data authentication operations. When a transmission has been received, the payer system's security unit 44 decrypts each message in the transmission that has been encrypted, using the receiving payer's private key. The payer system's security unit 44 also validates any message signatures that are present, and validates any image signatures that are present within each message. Each of the operations performed by the security unit 44 after a transmission has been received are described in detail below.

The payer management unit 56 creates and maintains a set of data structures within the payer system 50 as will be described below. In the preferred embodiment, the payer management unit 56 is a sequence of computer program steps stored in the memory 26. In response to a transmission request generated by the payer interface unit 52, the payer management unit 56 sends the transmission request to the provider system 12 specified in the transmission request using the payer system's data transmission/reception device 24. Via its data transmission/reception device 24, the payer system 50 receives transmissions from one or more provider systems 12. Data associated with a transmission is initially stored in the payer system's communications memory 34. Upon receiving a transmission, the payer management unit 56 determines whether the data is organized in a standard format. If so, the payer management unit 56 removes the standard formatting.

Figure 11:
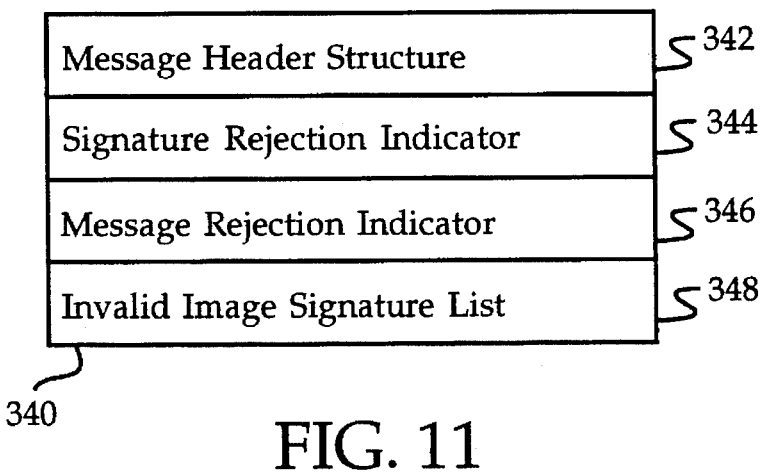
FIG. 11 is a block diagram of a received message relation structure of the present invention.

For each message within a received transmission, the payer management unit 56 creates a received message relation structure 340. Referring now to FIG. 11, a block diagram of a received message relation structure 340 is shown. The received message relation structure 340 is a data structure having a first data field 342 for storing a message header structure 180 received; a second data field 344 for storing a signature rejection indicator, used for security purposes and described in detail below; a third data field 346 for storing a message rejection indicator; and a fourth data field 348 for storing an invalid image signature list. In the preferred embodiment, the invalid image signature list specifies the image ID of each image in the message not having a valid image signature.

Figure 8B:
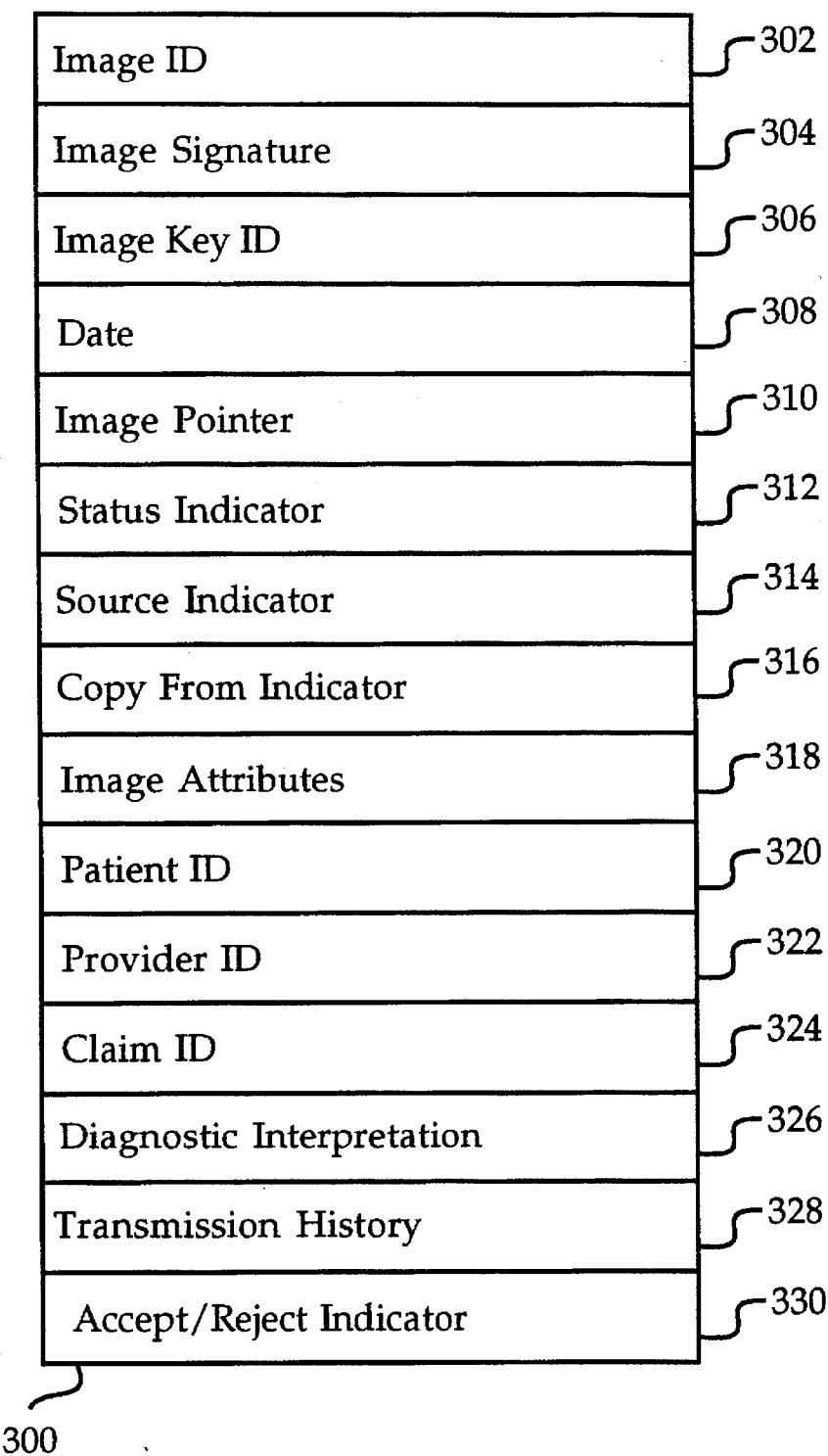
FIG. 8B is a block diagram of a payer-side image relation structure of the present invention.

After creating a received message relation structure 340 associated with a given message, the payer management unit 56 creates a payer-side image relation structure 300 for each image attachment structure 140 within the message. Referring now to FIG. 8B, a block diagram of a preferred embodiment of a payer-side image relation structure 300 is shown. The payer-side image relation structure 300 is a data structure having many data fields similar to those in the provider-side image relation structure 100. For ease of understanding, like reference numbers are used for like data fields in FIGS. 8A and 8B. The payer-side image relation structure 300 has a first data field 302 for storing the image ID; a second data field 304 for storing the image signature; a third data field 306 for storing the image key ID; a fourth data field 308 for storing the date on which the image was signed; a fifth data field 310 for storing the image pointer that specifies the location of the image itself; a sixth data field 312 for storing the status indicator for the image; a seventh data field 314 for storing the source indicator for the image; and eighth data field 316 for storing the copy-from indicator for the image; a ninth data field 318 for storing the image attributes associated with the image; a tenth data field 320 for storing the patient ID; an eleventh data field 322 for storing the provider ID; a twelfth data field 324 for storing the claim ID; a thirteenth data field 326 for storing the diagnostic interpretation; a fourteenth data field 328 for storing the transmission history of the image; and a fifteenth data field 330 for storing an accept/reject indicator used for security purposes as described in detail below.

After creating each received message relation structure 340 and each payer-side image relation structure 300, the payer management unit 50 performs reception processing operations that determine whether the message as received should be accepted or rejected. In the message processing operations, the payer management unit 56 may generate one or more message rejection notifications, or one or more message acceptance notifications. The reception processing operations are described in detail in the description of FIGS. 19A and 19B below.

In the present invention, a transmission from a payer system 50 to a provider system 12 can be a message rejection notification, a message acceptance notification, or a patient information request message. The patient information request message is preferably generated by the payer interface unit 52 when a payer system user identifies a patient for which medical information is required.

Figure 12:
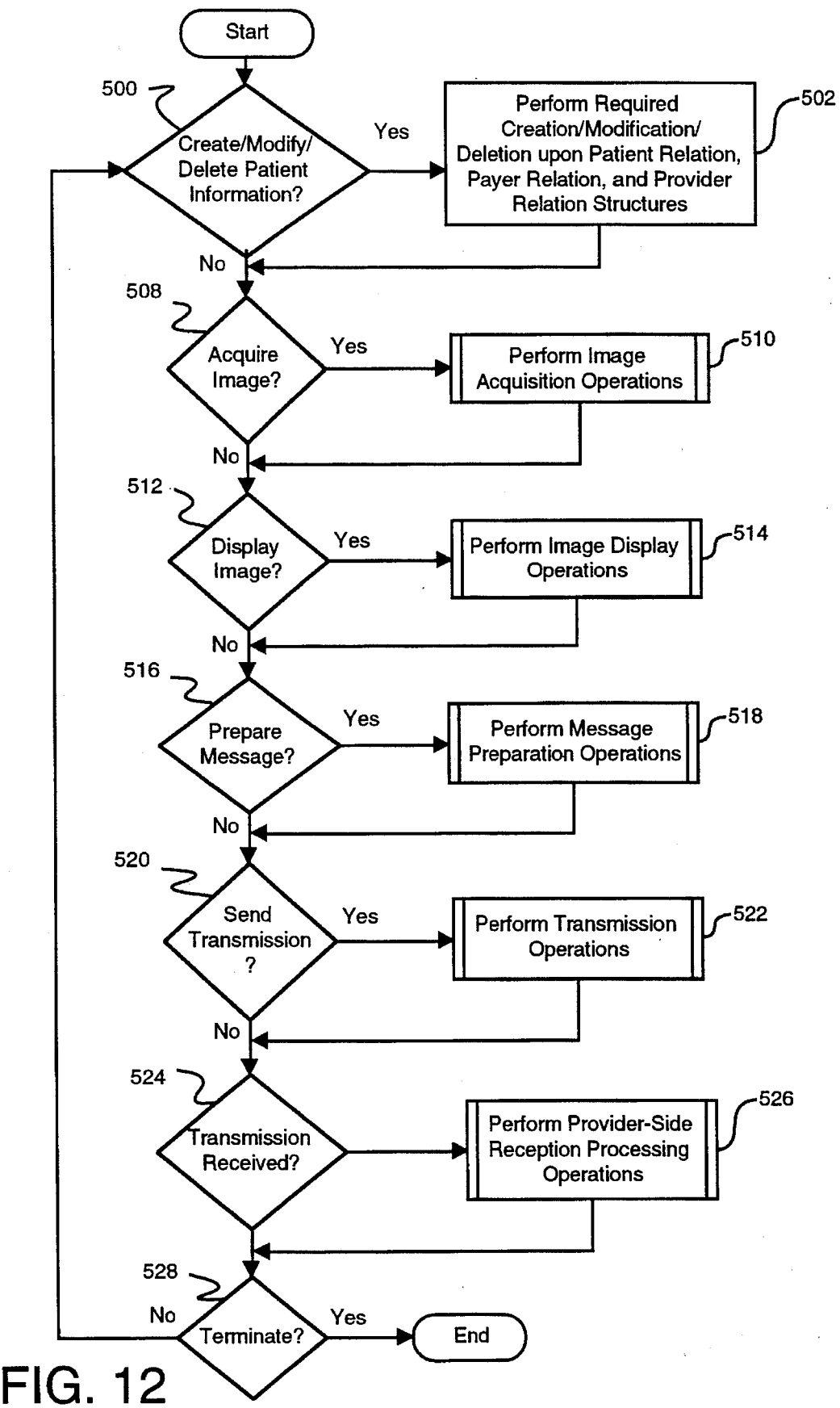
FIG. 12 is a flowchart of a preferred method for provider-side secure medical and dental record interchange in accordance with the present invention.

Referring now to FIG. 12, a flowchart of a preferred method for provider-side secure medical and dental record interchange is shown. The preferred method begins in step 500 with the provider management unit 46 determining whether patient-related information is to be created, modified or deleted. If so, the provider management unit 46 performs the required patient information creation, modification, or deletion, respectively in step 502. The provider management unit performs step 502 by creating, modifying, or deleting the appropriate patient relation structure 60, payer relation structure 70, and/or provider relation structure 80. In step 502, if a patient, payer, and/or provider relation structure 80 is to be created, the provider management unit 46 allocates a portion of the memory for use in the relation memory 32, and directs the provider interface unit 42 in the acquisition of the contents of the patient relation structure 60, the payer relation structure 70, and/or the provider relation structure 80, respectively. If a patient, payer, and/or provider relation structure 60, 70, 80 is to be modified, the provider management unit 46 loads the respective patient, payer, and/or provider relation structure 60, 70, 80 into the relation memory 32 if it is not already present in the relation memory 32, and subsequently directs the provider interface unit 42 in the acquisition of any content modifications. If a patient, payer, and/or provider relation structure 60, 70, 80 is to be deleted, the provider management unit 42 directs the provider interface unit 42 in the identification of the patient, payer, and/or provider relation structure 60, 70, 80, respectively, to be deleted, after which the provider management unit 46 deletes the appropriate relation structure 60, 70, 80 from the relation memory 32 or from the data storage device 22.

Figure 16:
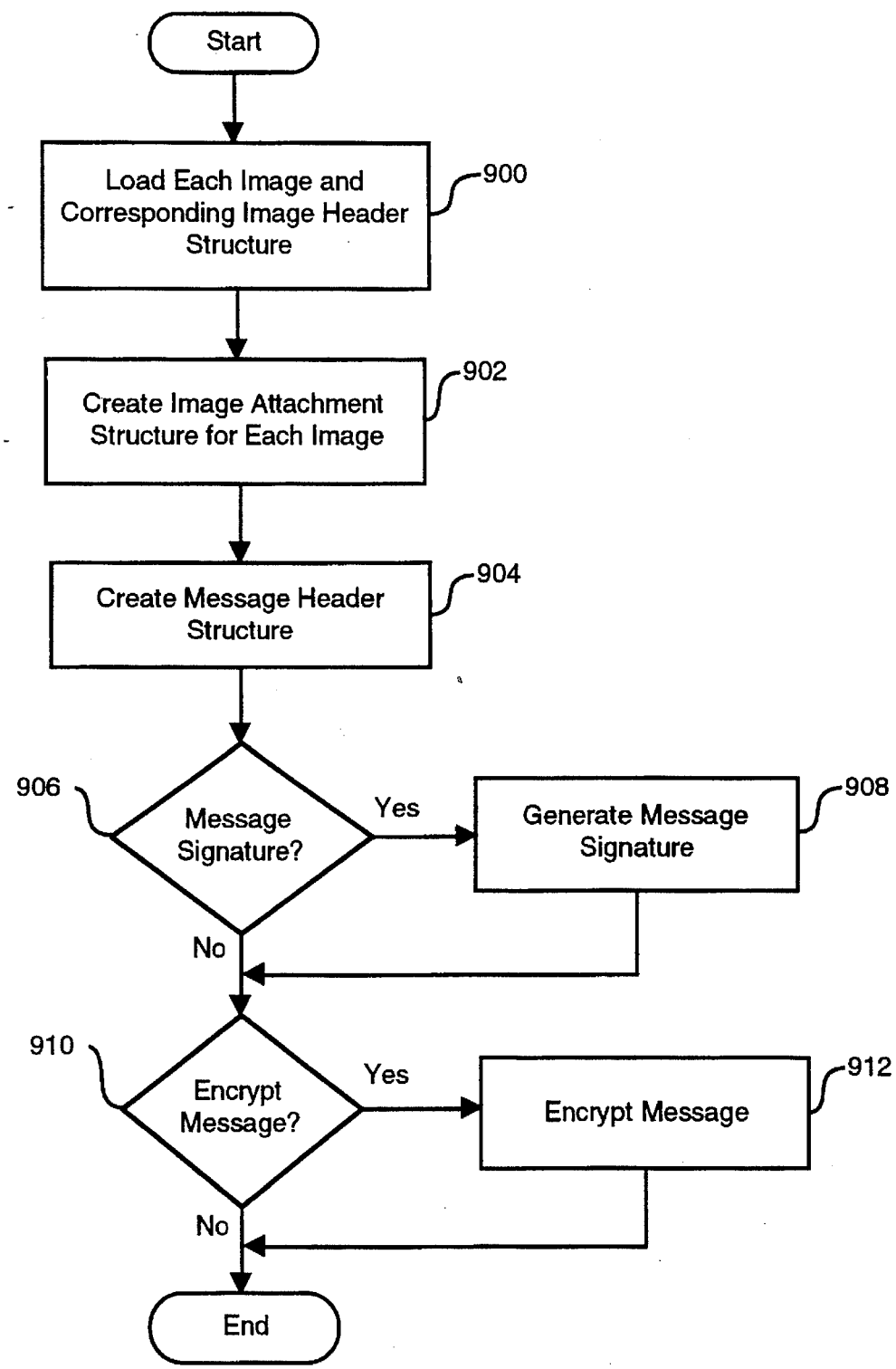
FIG. 16 is a flowchart of a preferred method for performing message preparation operations.

After step 502, or after step 500, the provider management unit 46 determines in step 508 whether an image is to be acquired. If an image is to be acquired, the provider management unit 46 performs image acquisition operations in step 510. The image acquisition operations are described in detail with reference to FIG. 13. Following step 510, or after step 508, the provider management unit 46 determines in step 512 whether the image is to be displayed. If the image is to be displayed, the provider management unit 46 performs image display operations in step 514. The image display operations are described in detail with reference to FIG. 14. Upon completion of step 514, or following step 512, the provider management unit 46 determines in step 516 whether a message is to be prepared. If so, the provider management unit 46 performs message preparation operations in step 518. In FIG. 16, the message preparation operations are described in detail. Following step 518, or after step 516, the provider management unit 46 determines whether a transmission is to be sent to a payer system 50 in step 520. In the preferred embodiment, the provider management unit 46 determines that a transmission is to be sent to a payer system in response to a transmission request, where the transmission request has been 1) generated by the provider interface unit 42 as a result of a provider action; or 2) received from the payer system 50. If a transmission is to be sent to a payer system, the provider management unit 46 performs transmission operations in step 522. The transmission operations are described in detail with reference to FIG. 17. After step 522, or after step 520, the provider management unit 46 determines whether a transmission from a payer system has been received in step 524. If so, the provider management unit 46 performs provider-side reception processing operations in step 526, as will be detailed below with reference to FIG. 18. Following step 526, or after step 524, the provider management unit 46 determines whether operation is to terminate in step 524. If operation is to terminate, the preferred method ends. If operation is to continue, the preferred method returns to step 500.

Figure 13:
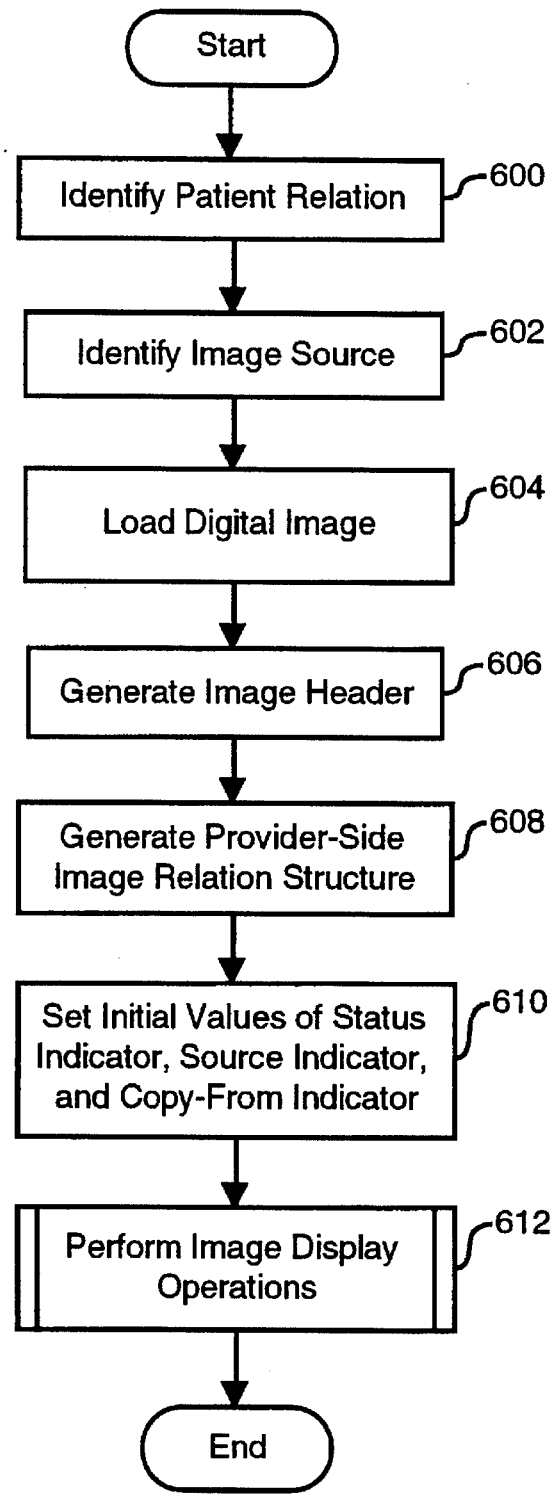
FIG. 13 is a flowchart of a preferred method for performing image acquisition operations.

Referring now to FIG. 13, a flowchart of a preferred method for performing image acquisition operations (step 510 of FIG. 12) is shown. The preferred method begins in step 600 with the provider management unit 46 identifying a patient relation structure 70 associated with an image acquisition request. Next, in step 602, the provider management unit 46 identifies the digital imager 20 specified in the image acquisition request. The provider management unit 46 then loads the image into the image memory 30 in step 604. Following step 604, the provider management unit 46 generates the image header structure 400 for the image. After generating the image header structure 400, the provider management unit 46 creates the provider-side image relation structure 100 in step 608, and then sets the initial values of the status indicator, the source indicator, and the copy-from indicator in step 610 in the manner previously described. After step 610, the provider management unit 46 performs image display operations in step 612, where the image display operations are described in detail with reference to FIG. 14.

Figure 14:
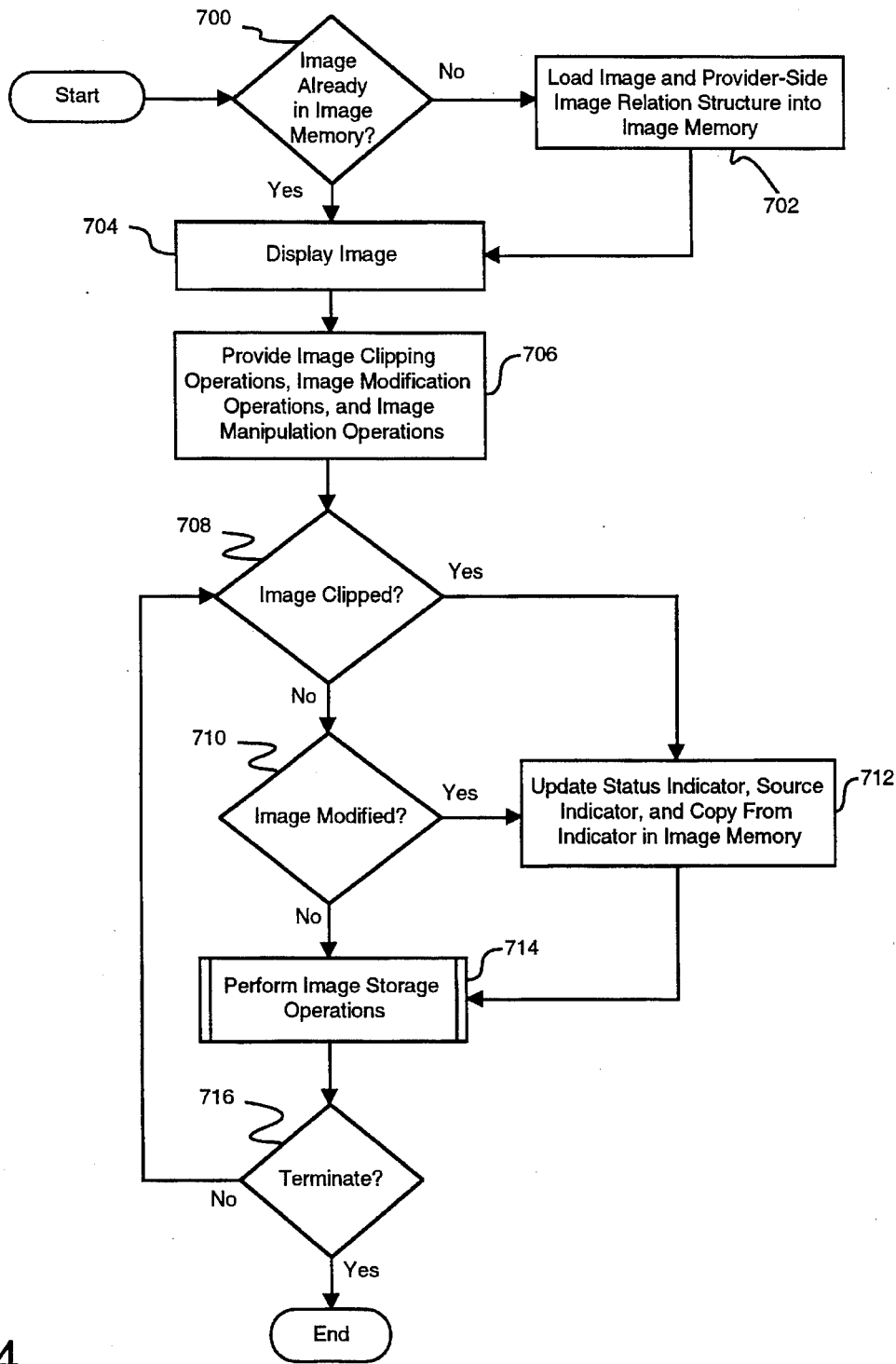
FIG. 14 is a flowchart of a preferred method for performing image display operations.

Referring now to FIG. 14, a flowchart of a preferred method for performing image display operations (step 514 of FIG. 12 and step 612 of FIG. 13) is shown. The preferred method begins in step 700 with the provider management unit 46 determining whether the image to be displayed is already present within the provider system's image memory 30. If not, the provider management unit 46 loads the required image and the corresponding provider-side image relation structure 100 into the image memory 30 in step 702. After step 702, or after step 700, the provider management unit 46 displays the image on the output device 18 in step 704. Next, the provider management unit 46 provides image clipping, image modification, and image manipulation operations in step 706. After step 706, the provider management unit 46 determines whether the image has been clipped in step 708. If so, the provider management unit 46 updates the status indicator in the corresponding image relation structure 100 present in the image memory 30 in step 712.

If in step 708 the provider management unit 46 determines that the image has not been clipped, the provider management unit 46 next determines in step 710 whether the image has been modified. If so, the provider management unit 46 updates the status indicator, the source indicator, and the copy-from indicator within the corresponding provider-side image relation structure 100 present in the provider system's image memory 30 in step 712. Following step 710 or step 712, the provider management unit 46 performs image storage operations in step 714. The image storage operations are described in detail with reference to FIG. 15 below. The provider management unit 46 then determines in step 716 whether display operations are to terminate. If display operations are to continue, the preferred method returns to step 700; otherwise, the preferred method ends.

Figure 15:
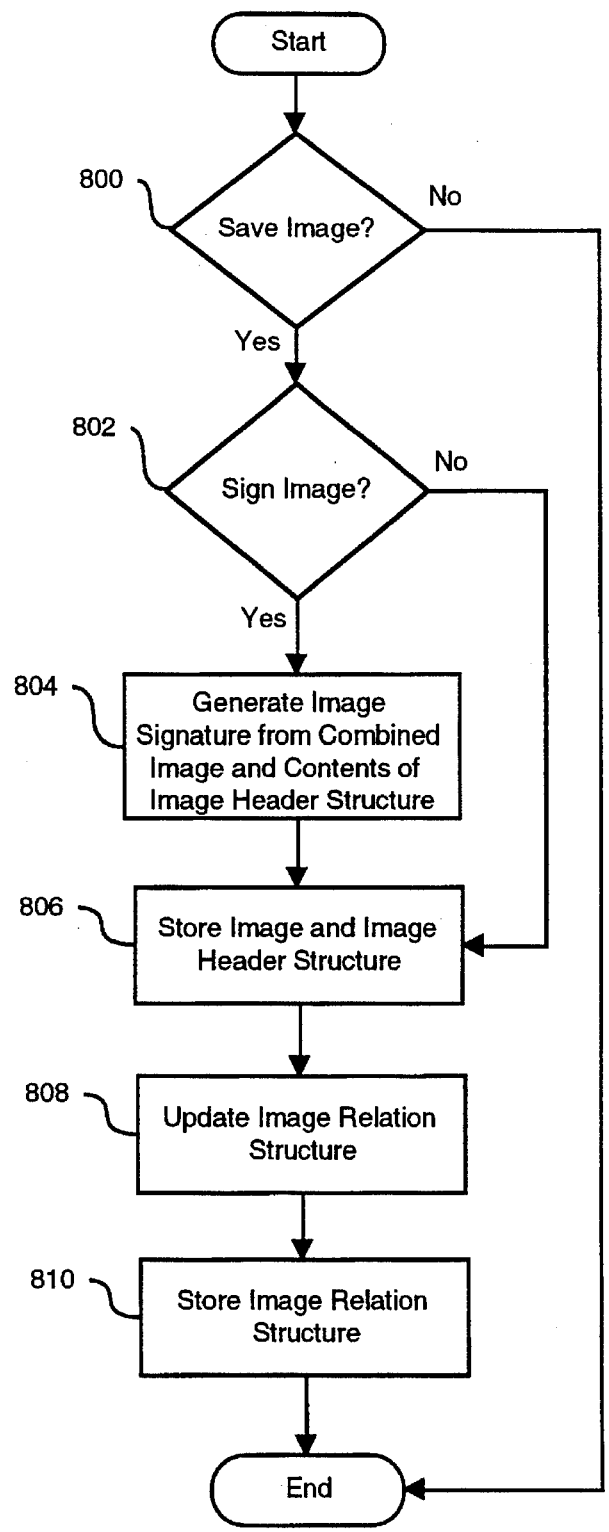
FIG. 15 is a flowchart of a preferred method for performing image storage operations.

Referring now to FIG. 15, a flowchart of a preferred method for performing image storage operations (step 714 of FIG. 14) is shown. The preferred method begins in step 800 with the provider management unit 46 determining whether the image is to be saved. If the image is not to be saved, the preferred method ends. If the image is to be saved, the provider management unit 46 determines in step 802 whether an image signature is to be generated in step 802. If an image signature is to be generated, the provider system's security unit 44 generates the image signature as the digital signature of the combined image and the contents of the image header structure 400 in step 804. After step 804, or after step 802, the provider management unit 46 stores the image and the image header structure 400 on the data storage device 22 in step 806. The provider management unit 46 next updates the image pointer and the image signature within the appropriate image relation structure 100 present in the payer system's image memory 30 in step 808. After step 808, the provider management unit 46 stores the image relation structure 100 on the data storage device 22 in step 810, after which the preferred method ends.

Referring now to FIG. 16, a flowchart of a preferred method for performing message preparation operations (step 518 of FIG. 12) is shown. Preferably, the provider management unit 46 performs the message preparation operations in response to a message preparation request. The preferred method begins in step 900 with the provider management unit 46 loading each image and each corresponding image header structure 400 associated with each image ID specified in the message preparation request into the communications memory. Next, the provider management unit 46 creates an image attachment structure 140 for each of the aforementioned images in step 902. After step 902, the provider management unit 46 creates a message header structure 180 in step 904. The provider management unit 46 then determines whether a message signature is to be generated in step 906. If so, the security unit 44 generates the message signature from the contents of each image header structure 400, each image attachment structure 140, and the fourth through the ninth data fields 188, 190, 192, 194, 196, 198 of the message header structure 180 using the private key associated with the preparing provider system user responsible for the message preparation request in step 908. After step 908, or after step 906, the provider management unit 46 determines whether the message is to be encrypted in step 910. If so, the security unit 44 encrypts the contents of each image header structure 400, each image attachment structure 140, and the fourth through the ninth data fields 188, 190, 192, 194, 196, 198 of the message header structure 180 using the public key associated with the payer to which the message is directed in step 912. Following step 912, or after step 910, the preferred method ends.

Figure 17:
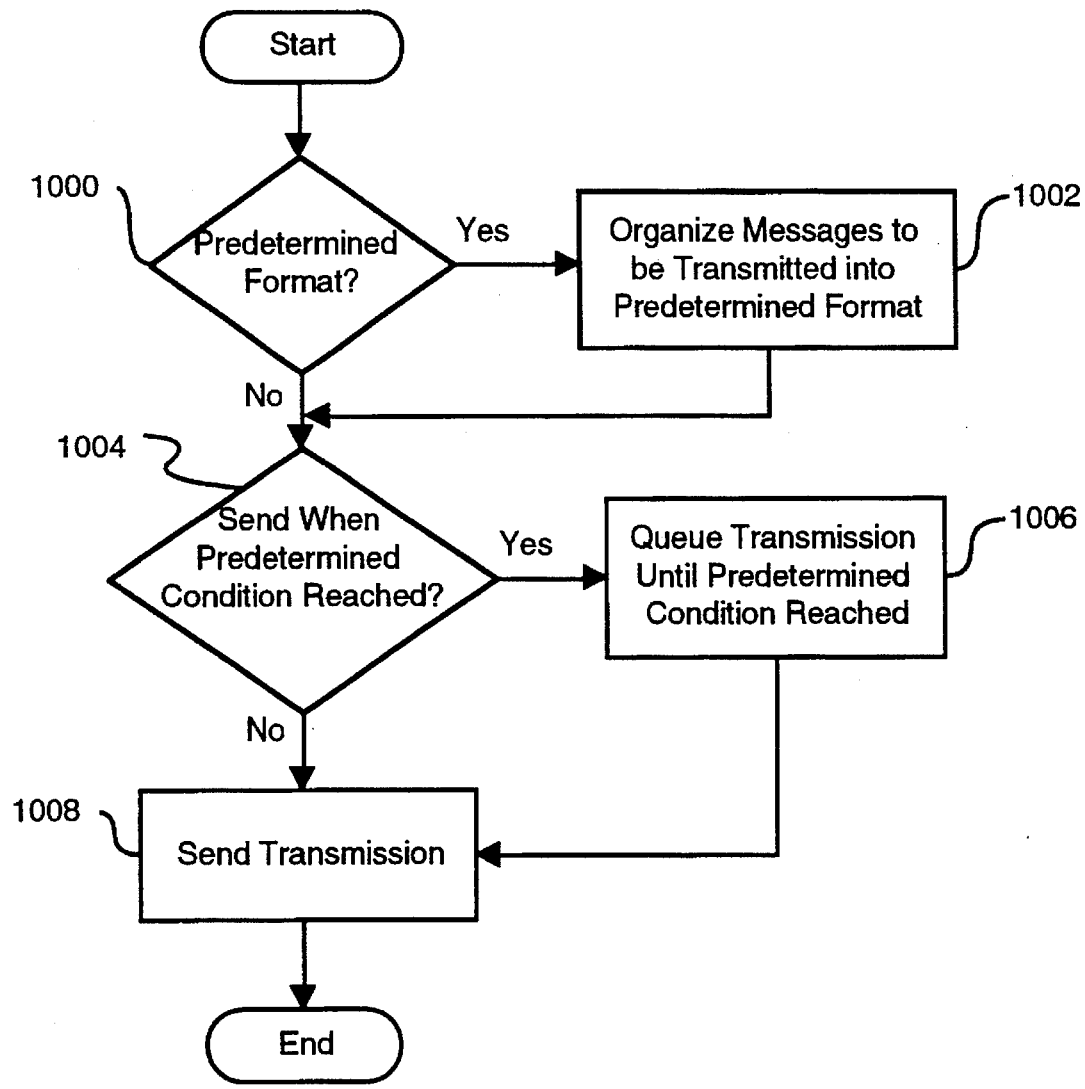
FIG. 17 is a flowchart of a preferred method for performing transmission operations.

Referring now to FIG. 17, a flowchart of a preferred method for performing transmission operations (step 522 of FIG. 12) is shown. In the preferred embodiment, the transmission operations are performed in response to a transmission request. The preferred method begins in step 1000 with the provider management unit 46 determining whether the transmission is to be organized into a predetermined format. If so, the provider management unit 46 organizes the transmission into the predetermined format in step 1002. After step 1002, or after step 1000, the provider management unit 46 determines whether the transmission is to be sent to the payer system 50 based upon a predetermined condition in step 1004. If so, the provider management unit 46 queues the transmission for sending until the predetermined condition is satisfied in step 1006. After step 1006, or after step 1004, the provider management unit 46 sends the transmission to the payer system 50 corresponding to the payer ID specified in the transmission request in step 1008. Preferably, the transmission includes each message currently residing in the communications memory 34. After step 1008, the preferred method ends.

Figure 18:
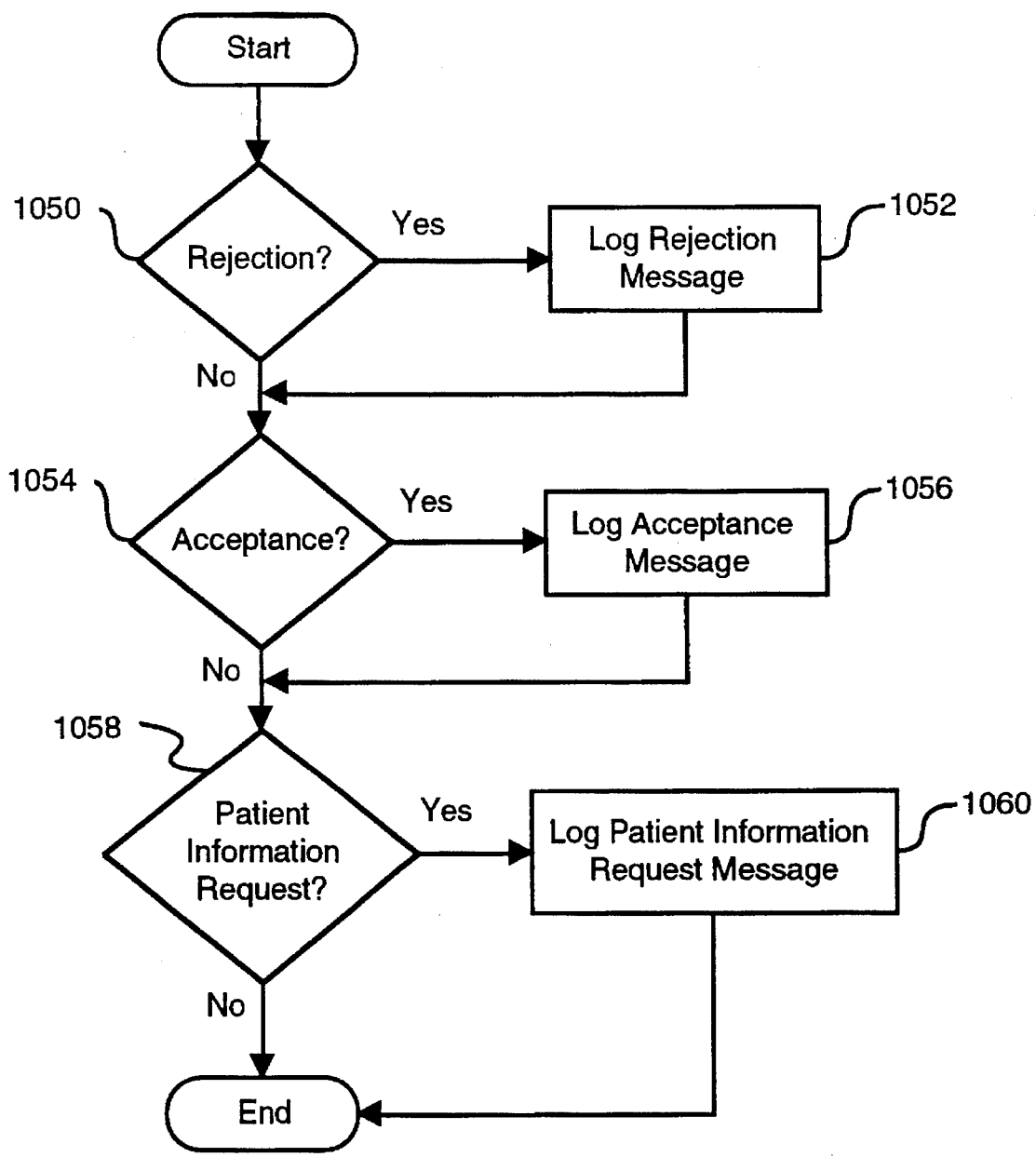
FIG. 18 is a flowchart of a preferred method for performing provider-side reception processing operations.

Referring now to FIG. 18, a flowchart of a preferred method for performing provider-side reception processing operations (step 526 of FIG. 12) is shown. The preferred method begins in step 1050 with the provider management unit 46 determining whether a message rejection notification has been received. If so, the provider management unit 46 logs the message rejection notification in the memory 26 in step 1052. After step 1052, or after step 1050, the provider management unit 46 determines whether a message acceptance notification has been received in step 1054. If a message acceptance notification has been received, the provider management unit 46 logs the message acceptance notification in the memory 26 in step 1056. Following step 1056, or following step 1054, the provider management unit 46 determines whether a patient information request message has been received in step 1058. If so, the provider management unit 56 logs the patient information request message in the memory 26 in step 1060. In the preferred method, the provider system management unit 46 interprets the patient information request message as a transmission request. Upon completion of step 1060, or after step 1058, the preferred method ends.

Figure 19A:
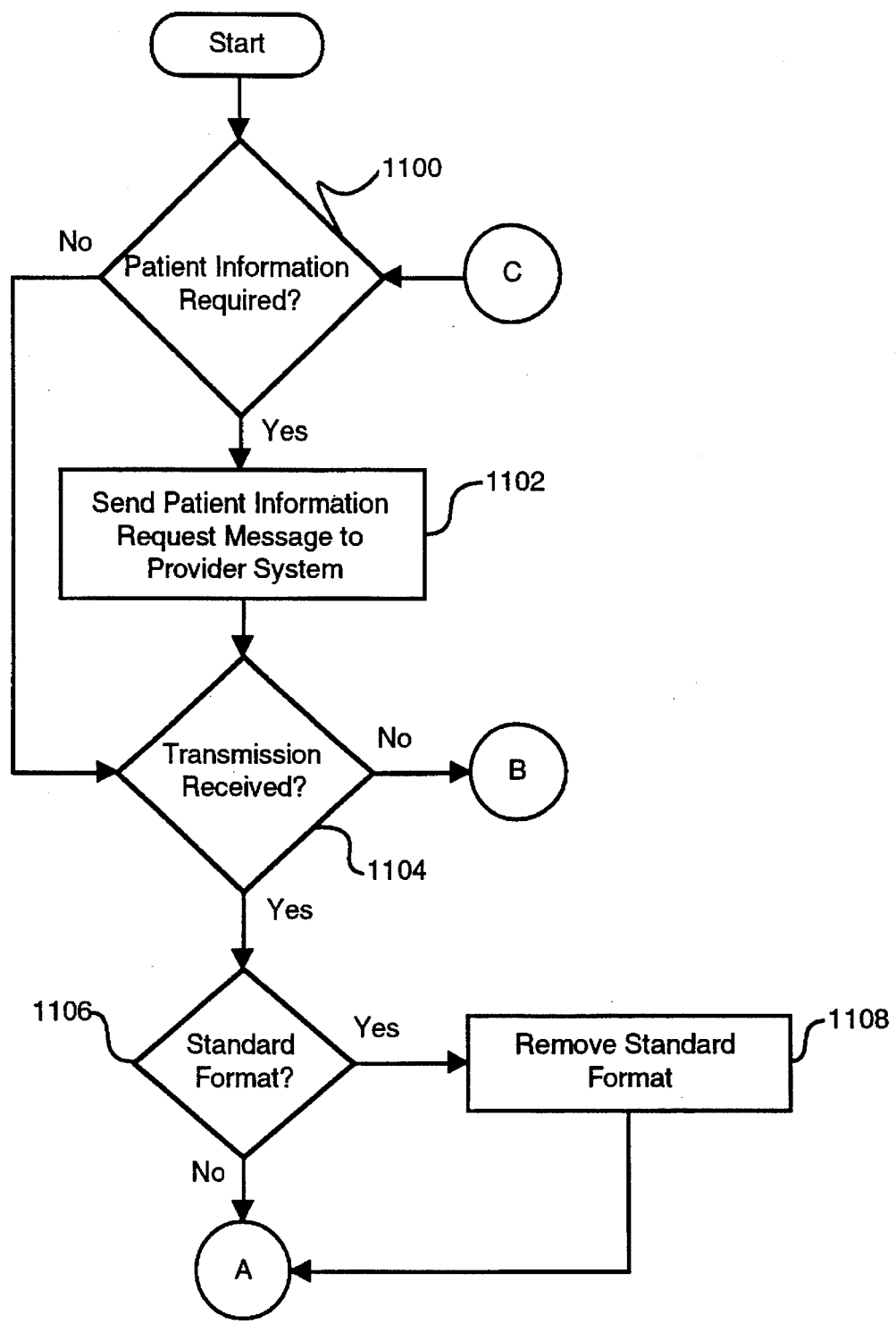
FIGS. 19A and 19B are a flowchart of a preferred method for payer-side secure medical and dental record interchange in accordance with the present invention.
Figure 19B:
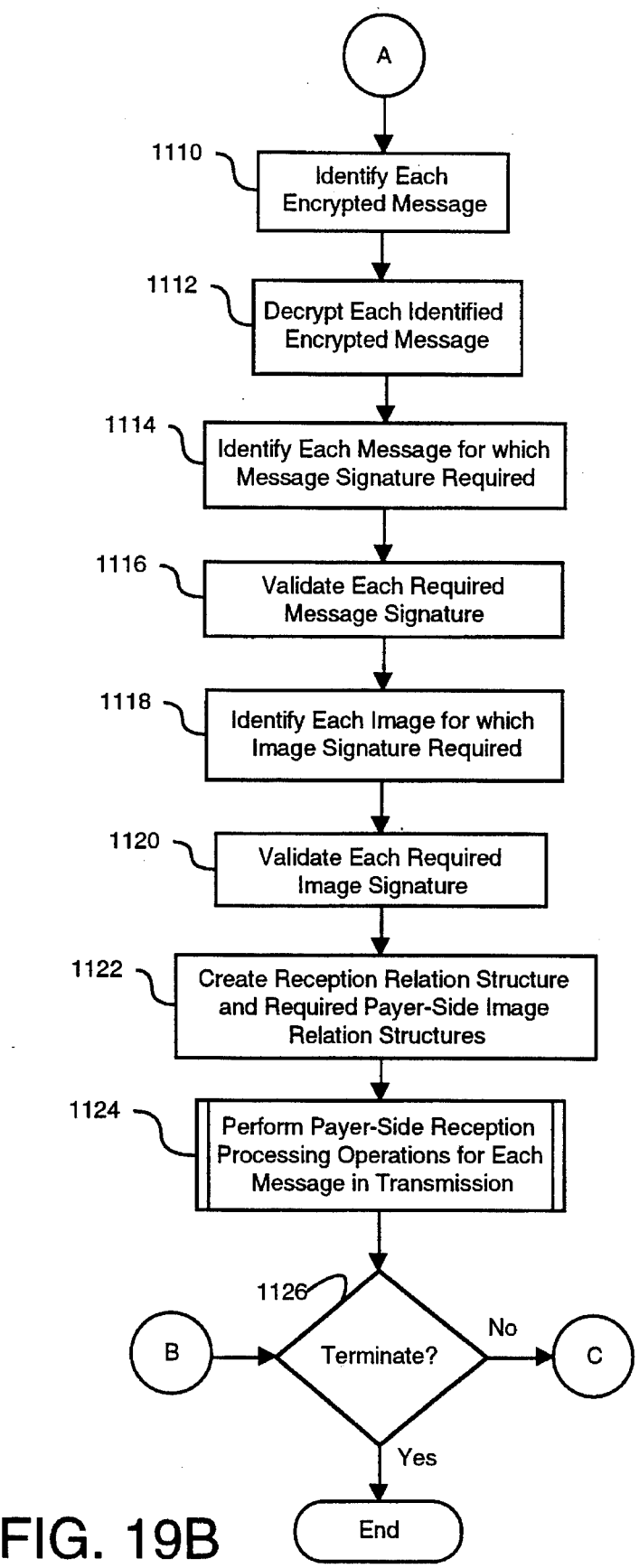

Referring now to FIGS. 19A and 19B, a flowchart of a preferred method for payer-side secure medical and dental record interchange is shown. The preferred method begins in step 1100 with the payer management unit 56 determining whether medical information associated with one or more patients is required from a particular provider system 12. Preferably, the payer management unit 56 determines that such medical information is required when the payer interface unit 52 generates a patient information request message in response to a payer system user action that specifies: 1) a particular provider system 12 as a transmission source; and 2) one or more patients. If patient information is required, the payer management unit 56 next sends a patient information request message to the specified provider system 12 via the payer system's data transmission/reception device 24 in step 1102.

After step 1102, or after step 1100, the payer management unit 56 next determines in step 1104 whether a transmission has been received from a provider system 12. If not, the preferred method proceeds to step 1126. In the event that a transmission has been received, the payer management unit 56 determines in step 1106 whether the received transmission has been organized into a standard format. If so, the payer management unit 56 removes the standard formatting in step 1108. After step 1106, or after step 1108, the payer management unit 56 identifies each message within the received transmission that is encrypted in step 1110. Next, the security unit 44 within the payer system 50 decrypts each identified encrypted message in step 1112. In step 1112, if a message cannot be successfully decrypted, the payer system's security unit 44 stores a reference to the message in the payer system's memory 26. Following step 1112, the payer management unit 56 identifies each message for which a message signature is required by the payer or by the provider in step 1114. Next, in step 1116, the payer system's security unit 44 validates each required message signature. In step 1116, if a message signature cannot be successfully validated, the security unit 44 stores a reference to the corresponding message in the payer system's memory 26. Next, the payer management unit 56 identifies each image within the transmission for which the payer requires an image signature in step 1118. Following step 1118, the payer system's security unit 44 validates each identified image signature step 1120. In step 1120, if an image signature cannot be successfully validated, the payer system's security unit 44 stores the image ID in the payer system's memory 26. Following step 1120, the payer management unit 56 creates a received message relation structure 340 and for each image in the transmission creates a payer-side image relation structure 300 in step 1122. Next, in step 1124, the payer management unit 56 performs payer-side reception processing operations for each message in the transmission. After step 1124, the payer management unit 56 determines whether operation is to terminate in step 1126. If operation is to continue, the preferred method returns to step 1100. If operation is to terminate, the preferred method ends.

Figure 20A:
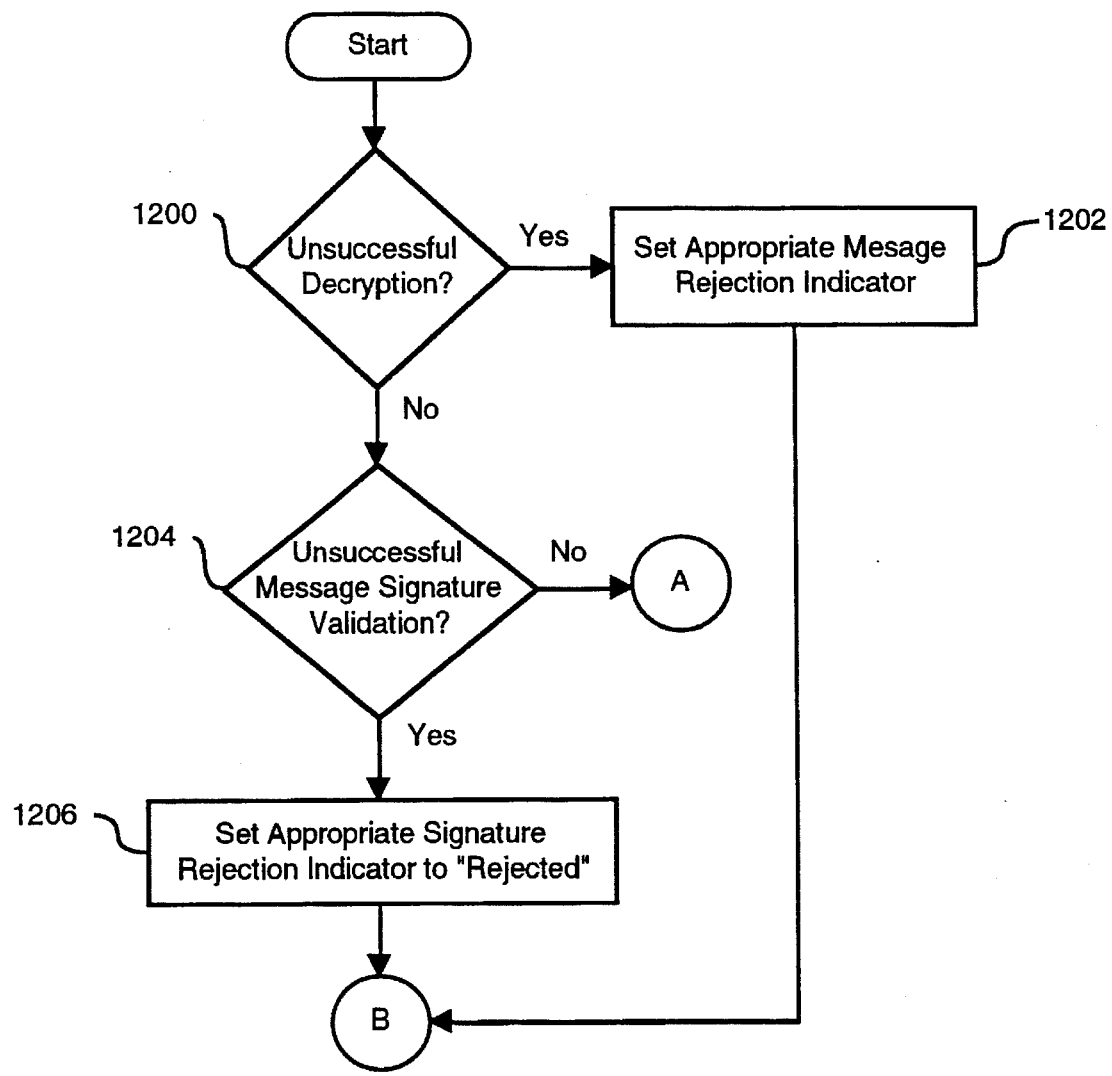
FIGS. 20A and 20B are a flowchart of a preferred method for performing payer-side reception processing operations.
Figure 20B:
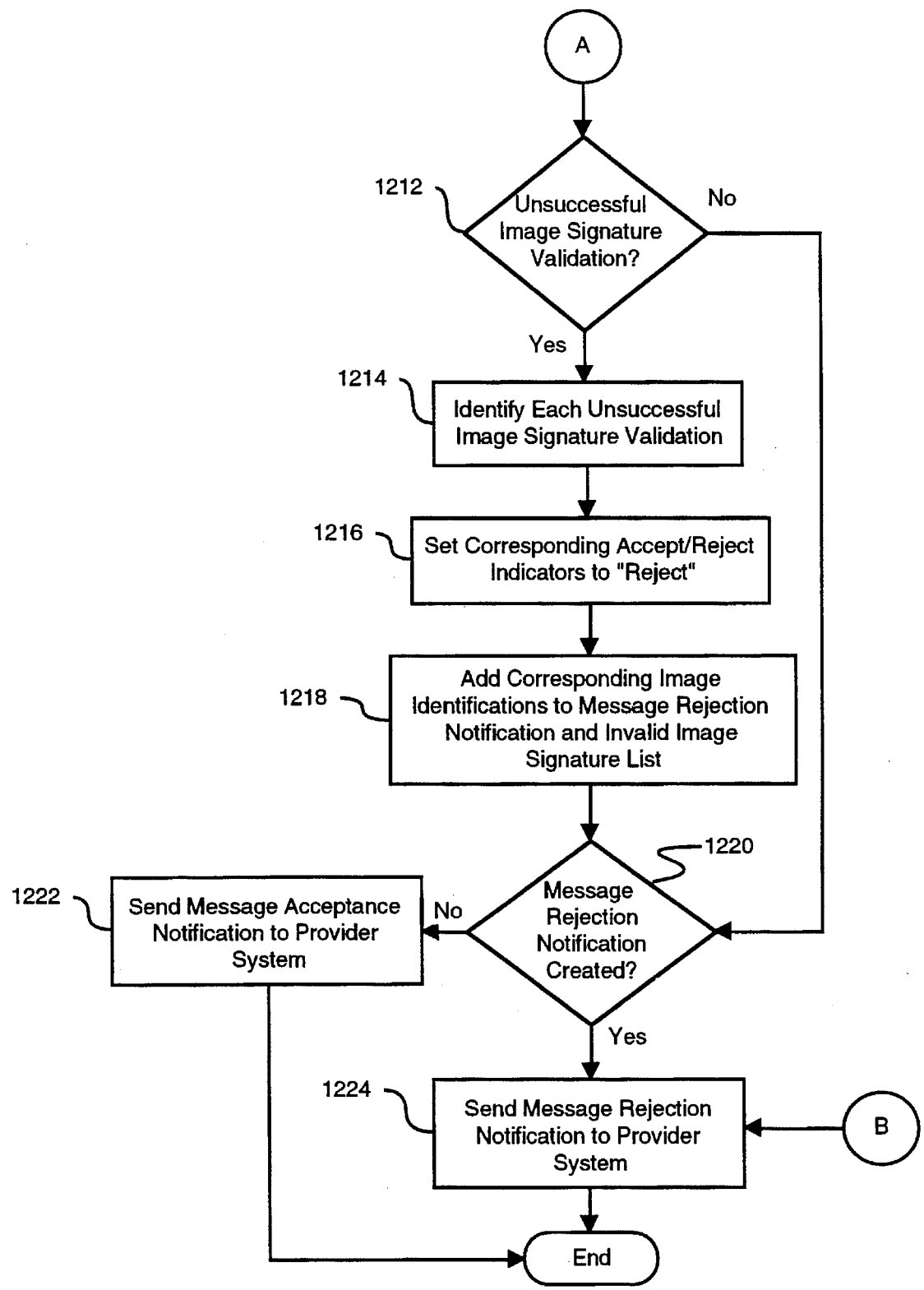

Referring now to FIGS. 20A and 20B, a flowchart of a preferred method for performing payer-side reception processing operations (step 1124 of FIG. 18B) is shown. The payer-side reception processing operations are preferably performed for each message in the transmission. The preferred method begins in step 1200 with the payer management unit 56 determining whether a message decryption performed by the security unit 44 within the payer system 50 was unsuccessful. If so, the payer management unit 56 sets the message rejection indicator in the appropriate received message relation structure 340 in step 1202, after which the preferred method proceeds to step 1224.

If the message decryption was successful, or if no message decryptions was required, the payer management unit 56 next determines whether a required message signature validations was unsuccessful in step 1204. If not, the preferred method proceeds to step 1212. If the message signature validations was unsuccessful, the payer management unit 56 next sets the signature rejection indicator in the received message relation structure 340 corresponding to the message to "rejected" in step 1206. After step 1206, the preferred method proceeds to step 1224.

In step 1212, the payer management unit 50 determines whether any required image signature validations were unsuccessful. If not, the preferred method proceeds to step 1220. In the event that one or more image signature validations were unsuccessful, the payer management unit 50 next identifies each required image signature validation that was unsuccessful in step 1214. For each required image signature validation identified as unsuccessful, the payer management unit 50 sets the accept/reject indicator in the corresponding payer-side image relation structure 300 corresponding to each image for which a required image signature was not successfully validated to "reject" in step 1216. Next, in step 1218, the payer management unit 56 adds the image ID of each image having a required but unsuccessfully validated image signature to a message rejection notification, and to the invalid image signature list in the fourth data field 348 of the appropriate received message relation structure 340.

Following step 1218, or after step 1212, the payer management unit 50 determines whether a message rejection notification has been created in step 1220. If no message rejection notification has been created, the payer management unit 50 sends a message acceptance notification to the provider system 12 that sent the transmission in step 1222. If a message rejection notification has been created, the payer management unit 50 sends the message rejection notification to the provider system 12 that sent the transmission in step 1224. After step 1222, or after step 1224, the preferred method ends.

Through the use of the image ID, the image signature, the status indicator, the source indicator, the copy-from indicator, and the message signature described above, the present invention greatly increases the level of security involved in medical and dental record interchange. In particular, the present invention provides a means by which a medical claim payment authority can successfully detect the presence of an altered image within a transmission, and whether a particular image is actually associated with a given patient. The use of image signatures and message signatures further enhances the level of security involved in medical and dental record interchange by associating an image or a message, respectively, with a particular provider in a secure manner. The generation of an image signature provides a means by which the provider associated with the private key used to encrypt the image digest may be held legally responsible for the authenticity of the image. Those skilled in the art will recognize that the present invention is applicable not only to images, but to any type of medical information in general.

While the present invention has been described with reference to certain preferred embodiments, those skilled in the art will recognize that various modifications may be provided. For example, the digital imager 20 could be a computed tomograph system or a magnetic resonance imaging system. As another example, a provider system could be implemented as a single mainframe computer within a hospital. In a like manner, a payer system could be implemented as a mainframe computer utilized by an insurance company. These and other variations upon and modifications to the preferred embodiments are provided for by the present invention, which is limited only by the following claims.

What is claimed is:

1. A system for secure medical and dental record communication comprising:

a provider system having a processing unit, a digital imager, a data transmission/reception device, and a memory wherein a provider management unit resides, for generating a unique image identification associated with an image, creating a message that includes the image, and sending the message to a payer system; and a payer system having a processing unit, a data transmission/reception device, and a memory wherein a payer management unit resides, for selectively requesting a transmission that includes the message from the provider system, receiving the message from the provider system, performing record evaluation and processing, and selectively generating a message acceptance notification or a message rejection notification.

2. The system of claim 1, wherein the image identification comprises a date upon which the image was captured, a time at which the image was captured, and a unique provider system serial number.

3. The system of claim 1, wherein the provider system further comprises an image relation structure having a status indicator corresponding to a manner in which the image has been acquired.

4. The system of claim 1, wherein the provider system further comprises an image relation structure having a source indicator corresponding to the digital imager.

5. The system of claim 1, wherein the provider system further comprises an image relation structure having a copy-from indicator corresponding to whether the image is an original or a copy.

6. The system of claim 1, wherein the provider system sends the message to the payer system in response to a transmission request received from the payer system.

7. The system of claim 1, wherein the provider system memory further includes a security unit, for generating an image signature associated with the image and for generating a message signature associated with the message.

8. The system of claim 7, wherein the payer system memory further includes a security unit, for validating the message signature to determine the authenticity of the message and for validating the image signature to determine the authenticity of the image.

9. A provider system for secure medical and dental record communication with a payer system, wherein the payer system performs record evaluation and processing, the provider system comprising:

a processing unit having an input and an output, for executing computer program steps;

a digital imager having an output, the digital imager for capturing an image;

a memory wherein a provider management unit resides, the memory having an input and an output, the provider management unit controlling the generation of an image identification corresponding to the image, the creation of an image relation structure having a status indicator that corresponds to a manner in which the image was acquired, and the generation of a message that includes the image, the input of the memory coupled to the output of the processing unit and to the output of the digital imager, the output of the memory coupled to the input of the processing unit; and a data transmission/reception device having an input, for transmitting and receiving data between the payer system and a provider system, the input of the data transmission/reception device coupled to the output of the memory and to the output of the processing unit.

10. The system of claim 9, wherein the memory further includes a security unit having an input and an output, for generating an image signature, the input of the security unit coupled to the input of the memory, the output of the security unit coupled to the output of the memory; and wherein the provider management unit has an input and an output, the input of the provider management unit coupled to the input of the memory, and the output of the provider management unit coupled to the output of the memory.

11. The system of claim 10 wherein the image signature is a digital signature corresponding to the combination of the image and the image identification.

12. A payer system for performing record evaluation and processing and for secure medical and dental record communication with a provider system, the payer system comprising:

a processing unit having an input and an output, for executing computer program steps;

a memory wherein a payer management unit resides, the memory having an input and an output, the payer management unit selectively requesting from a provider system a message having an image, and selectively generating; a message acceptance notification or a message rejection notification, the input of the memory coupled to the output of the processing unit, the output of the memory coupled to the input of the processing unit; and a data transmission/reception device having an input, for transmitting and receiving data between the payer system and a provider system, the input of the data transmission/reception device coupled to the output of the memory and to the output of the processing unit.

13. The system of claim 12, wherein the memory further includes a security unit having an input and an output, for verifying a message signature and for verifying an image signature, the input of the security unit coupled to the input of the memory, the output of the security unit coupled to the output of the memory; and wherein the payer management unit has an input and an output, the input of the payer management unit coupled to the input of the memory, the output of the payer management unit coupled to the output of the memory.

14. A means for secure medical and dental record communication comprising:

a means for capturing an image;

a means for generating an image identification corresponding to the image; and a means for associating a status indicator with the image, the status indicator corresponding to a manner in which the image was captured; and a means for sending the image to a payer system for record evaluation and processing.

15. The means of claim 14, further comprising a means for associating a source indicator with the image, the source indicator corresponding to a digital imager from which the image was captured.

16. The means of claim 14, further comprising a means for associating a copy-from indicator with the image, the copy-from indicator corresponding to whether the image is an original.

17. The means of claim 14, further comprising a means for generating an image signature, the image signature being a digital signature corresponding to the combination of the image and the image identification.

18. The means of claim 17, further comprising:

a means for requesting a transmission from a provider system, the transmission including an image associated with a patient;

a means for validating an image signature; and a means for generating one from the set of a message acceptance notification or a message rejection notification according to whether an image signature validation is successful.

19. A method for provider-side medical and dental record communication for a provider system having a processing unit and a memory wherein a provider management unit and a security unit reside, the method comprising the steps of:

capturing an image;

generating a unique image identification corresponding to the image; and creating an image relation structure corresponding to the image, the image relation structure including a status indicator corresponding to a manner in which the image was captured.

20. The method of claim 19, wherein the image relation structure further includes a source indicator, the source indicator corresponding to a digital imager.

21. The method of claim 19, wherein the image relation structure further includes a copy-from indicator, the copy-from indicator corresponding to whether the image is an original or a copy.

22. The method of claim 19, further comprising the step of generating an image signature, the image signature being a digital signature for the combination of the image and the image identification.

23. The method of claim 19, further comprising the steps of:
  creating a message that includes the image; and
  generating a message signature, the message signature being a digital signature corresponding to the message.

24. A method for payer-side medical and dental record communication for a payer system which performs record evaluation and processing and having a processing unit and a memory wherein a payer management unit and a security unit reside, the method comprising the steps of:
  receiving a message from a provider system;
  validating a message signature; and
  generating one from a group consisting of:
    a message rejection notification in the event that the message signature validation is unsuccessful; and
    a message acceptance notification in the event that the message signature validation is successful.

25. A method for payer-side medical and dental record communication for a payer system which performs record evaluation and processing and having a processing unit and a memory wherein a payer management unit and a security unit reside, the method comprising the steps of:
  receiving a message from a provider system, the message including an image having a corresponding image signature;
  validating an image signature; and
  generating one from a group consisting of:
    a message rejection notification in the event that the image signature validation is unsuccessful; and
    a message acceptance notification in the event that the image signature validation is successful.

26. A method for payer-side medical and dental record communication for a payer system which performs record evaluation and processing and having a processing unit and a memory wherein a payer management unit and a security unit reside, the method comprising the steps of:
  receiving a message from a provider system, the message having a message signature and including an image having a corresponding image signature;
  validating the message signature;
  validating each image signature associated with the message; and
  generating a message acceptance notification in the event that the message signature validation and each image signature validation is successful.

* * * * *